United States Patent [19]

DeGraw et al.

[11] Patent Number: 5,536,724

[45] Date of Patent: Jul. 16, 1996

[54] ANTIINFLAMMATORY AND ANTINEOPLASTIC 5-DEAZAAMINOPTERINS AND 5,10-DIDEAZAAMINOPTERINS

[75] Inventors: Joseph I. DeGraw, Sunnyvale; William T. Colwell, Menlo Park, both of Calif.; Francis M. Sirotnak, New York, N.Y.; R. Lane Smith, Palo Alto, Calif.; James R. Piper, Birmingham, Ala.

[73] Assignees: SRI International, Menlo Park, Calif.; Sloan-Kettering Institute, New York, N.Y.

[21] Appl. No.: 140,793

[22] Filed: Oct. 21, 1993

Related U.S. Application Data

[63] Continuation-in-part of Ser. No. 90,750, Jul. 12, 1993, Pat. No. 5,354,751, which is a continuation-in-part of PCT/US93/03965 filed Apr. 28, 1993, which is a continuation-in-part of Ser. No. 28,431, Mar. 9, 1993, Pat. No. 5,374,726, and a continuation-in-part of Ser. No. 8,919, Jan. 26, 1993, abandoned, and a continuation-in-part of Ser. No. 938,105, Aug. 31, 1992, abandoned, and a continuation-in-part of Ser. No. 845,407, Mar. 3, 1992, abandoned, and a continuation-in-part of Ser. No. 875,779, Apr. 29, 1992, abandoned.

[51] Int. Cl.$^6$ .................... A61K 31/505; C07D 471/04; C07D 333/38; C07D 213/81
[52] U.S. Cl. .................................... 514/258; 544/279
[58] Field of Search ........................... 544/279; 514/258

[56] References Cited

U.S. PATENT DOCUMENTS

| | | | |
|---|---|---|---|
| 4,725,687 | 2/1988 | Piper | 544/239 |
| 5,077,404 | 11/1991 | Piper | 544/250 |
| 5,260,296 | 11/1993 | Nair et al. | 514/249 |

OTHER PUBLICATIONS

Piper, Chem Abs 109, 170844 (1988).
Schnur, J Med Chem 34, 914–918 (1991).
DeGraw, J Med Chem 33, 673–677 (1990).
Piper, J Med Chem 35, 332–337 (1992).
Sirtroak, Cancer Res 48, 5686 (1988).
Piper, J. R., et al., Studies Aided by Molecular Graphics of Effects of Structural Modifications on the Binding of Antifolate Inhibition to Human Dihydrofolate Reductase, Preclinical Pharmacology/Experimental Therapeutics Section, *Proceedings of the American Association for Cancer Research*, vol. 33, 2459–412 (Mar. 1992) Abstract 2459.

*Primary Examiner*—Mark L. Berch
*Attorney, Agent, or Firm*—Hana Verny

[57] ABSTRACT

Antiinflammatory and antineoplastic 5-deazaaminopterins and 5,10-dideazaaminopterins and their 5 and 10 alkyl analogs. A method for the treatment and prevention of inflammatory disease, such as rheumatoid arthritis, and for suppression and prevention of neoplastic growth in tumors and in blood forming tissues. A process for preparation of 10-deazaaminopterins.

24 Claims, No Drawings

ANTIINFLAMMATORY AND ANTINEOPLASTIC 5-DEAZAAMINOPTERINS AND 5,10-DIDEAZAAMINOPTERINS

This is application is a continuation-in-part of the U.S. patent application for "Novel Antiinflammatory and Antineoplastic 10-Deazaaminopterins", Ser. No. 08/090,750, U.S. Pat. No. 5,354,751 filed on Jul. 12, 1993 which is a continuation-in-part of the PCT application U.S. Ser. No. 93/03965 filed on Apr. 28, 1993 entitled "Deazaaminopterins for Treatment of Inflammation", which is a continuation-in-part of the U.S. patent application for "Process for Preparing 10-Deazaaminopterins and 5,10- and 8,10-Dideazaaminopterins from Pteroic Dicarboxylic Acid Diesters", Ser. No. 08/028,431 filed on Mar. 9, 1993 U.S. Pat. No. 5,374,726 and of the U.S. patent application for "Heteroaroyl-10-Deazaaminopterins and 5,10-Dideazaaminopterins for Treatment of Inflammation", Ser. No. 08/008,919 filed on Jan. 26, 1993 abandoned and of the U.S. patent application for "Heteroaroyl-10-deazaaminopterins for Treatment of Inflammation", Ser. No. 07/938,105 filed on Aug. 31, 1992 abandoned and of the U.S. patent application for "10-Alkenyl and 10-Alkynyl-10-Deazaaminopterins," Ser. No. 07/845,407 abandoned filed on Mar. 3, 1992, and of the U.S. patent application for "5-Deazaaminopterins and 5,10-Dideazaaminopterins for Treatment of Inflammation, Ser. No. 07/875,779 filed on Apr. 29, 1992 abandoned.

BACKGROUND OF THE INVENTION

1. Field of the Invention

The current invention concerns novel antiinflammatory and antineoplastic 5-deazaaminopterins and 5,10-dideazaaminopterin compounds and their 5 and 10 alkyl analogs. In particular, the invention concerns 5-alkyl and heteroaroyl-5-deazaaminopterins and 5,10-dideazaaminopterins having antiinflammatory, antileukemic and antitumorigenic biological activity, as well as a method for treatment of inflammatory diseases, leukemia and tumors, pharmaceutical compositions and a process for preparation of these compounds.

2. Background of the Invention and Related Disclosures

Rheumatoid arthritis, malignant tumors and leukemia are severely debilitating diseases which are often fatal, as in cases of leukemia and malignant growths. Drugs which are currently available and used for treatment of these diseases typically have undesirable secondary symptoms or are highly toxic.

Rheumatoid arthritis is one of a number of forms of proliferative diseases. The development of drugs for amelioration or curing the disease has become of primary interest for many years. Until most recently such attempts were without appreciable success.

Rheumatoid arthritis is an inflammation of the joints arising from infectious, metabolic, or constitutional causes, usually of unknown origin. In its advanced stage it is debilitating, as it can result in serious restriction and impairment of movement and even in invalidism. Since rheumatoid arthritis is a common disease that affects 2-3 million people in the United States alone, it poses a serious health problem. With disease progression, a substantial proportion of affected individuals develop erosive joint disease and, despite therapies including disease-modifying antirheumatic drugs such as gold complexes, penicillamine and antimalarials often require surgical joint replacement. In some patients with intractable rheumatoid arthritis, administration of immunosuppressive agents including azathioprine, methotrexate, cyclophosphamide, and combinations of these drugs have been proven beneficial. However, the actual or potential side effects of some of these drugs, including bone marrow toxicity and neoplasia, have limited the frequency and the dose at which they can be administered.

Leukemia is an acute or chronic disease of unknown cause which is characterized by malignant neoplasm of the blood forming tissues in man and other warm-blooded animals. It is characterized by an abnormal increase in the number of immature leukocytes in the tissues of the body and in the circulating blood. The disease apparently affects the blood-forming organs, and is classified according to the type of leukocyte that is being proliferated abnormally. The disease is one of a number of forms of neoplastic disease, and the development of drugs for amelioration or curing the disease has been of great interest. Today, many forms of leukemia can be effectively treated with various drugs. In the case of combination chemotherapy with acute lymphocytic leukemia in children, a large percentage, of five year or longer survivals are obtained. The disease is now classified as curable. However, both the drugs or chemotherapy have very undesirable and debilitating effects and severe secondary symptoms on patients. Therefore, it would be highly advantageous to provide drugs or therapies which would avoid these secondary symptoms.

Malignant tumors typically result from a cellular malignancy whose unique characteristics—loss of normal cellular controls and regulations—results in unregulated growth, lack of differentiation, and ability to invade local tissues and metastasize.

There is no effective treatment of malignant growths aside from radical surgery. Moreover, once the tumor metastasizes, the only therapies which are somewhat effective are radiotherapy and chemotherapy. Both these therapies have severe side-effects which makes the recovery of the patients lengthy, complicated and overall very unpleasant.

It would thus be extremely useful to provide therapies for rheumatoid arthritis, leukemia and malignant tumors with drugs which would be less toxic and still be effective in treatment of these diseases.

The antifolic acid drug, methotrexate, has been used as an antitumor agent since 1955. Its cytotoxic action in tumors is related to its ability to inhibit, essentially irreversibly, the key enzyme, dihydrofolate reductase, required for biosynthesis of tetrahydrofolic acid. Tetrahydrofolate is a vital component in one-carbon metabolism in cells, being required for biosynthesis of purine and pyrimidine nucleosides of the DNA and RNA. Methotrexate is a powerful cytotoxic agent whose principal toxicities affect liver, kidney, and mucosal tissue. Liver toxicity particularly is the paramount concern for use of methotrexate in therapy of chronic diseases such as rheumatoid arthritis.

In 1974, *J. Med. Chem.*, 17:552 (1974) reported the synthesis and antifolate activity of 10-deazaaminopterin. The antimicrobial and antitumor activities of the powerful dihydrofolic reductase inhibitors aminopterin and its N-10-methyl derivative, methotrexate, are well known, and numerous attempts were made to prepare analogues having the improved potency, cell penetration and toxicity properties.

*J. Med. Chem.*, 25: 877–880 (1982), discloses a preparation of N-10 propyl, octyl, and propargyl analogues of methotrexate. Biological evaluations of the three compounds consisted of studies of their effects on inhibition of dihydrofolate reductase and thymidylate synthase, on L1210 cell growth inhibition, on cellular membrane transport with various murine cell types on in vivo activity in mice v. in vitro activity on L1210 leukemia and S180 ascites, and on plasma clearance in mice.

In 1983, *J. Org. Chem.*, 48:4852–4860 (1983) reported that L-5-deazaaminopterin in vitro is equipotent with methotrexate both as an inhibitor of bovine liver dihydrofolate reductase and of L1210 murine leukemia cells and in vivo both against L1210 and P388 leukemia in BDF$_1$ mice.

The preparation of 10-alkyl-8,10-dideazaaminopterin compounds as potential antitumor agents was described in *J. Med. Chem.*, 27: 376 (1984) and U.S. Pat. No. 4,460,591. While the process described there was useful in the synthesis of certain 10-alkyl-8,10-dideazaaminopterin analogs, it is not suitable for preparation of compounds where the 10-substituent is alkenyl or alkynyl and where a different pterin ring moiety is present (i.e., 2,4-diaminopteridine, 2,4-diamino-5-deazapteridine, etc.), or where the benzoate moiety is replaced by heteroaryl groups. The process generally lacks reproducibility and gives poor yields of impure products in the cyanide-mediated decarbomethoxylation step.

The ability of methotrexate to affect the inflammatory conditions of rheumatoid arthritis may be linked to its cytotoxic behavior. This may be in the nature of immune suppression and could involve attack on inflammatory phagocytic cells such as macrophages or neutrophils and T-helper cells in the synovial region. Very few methotrexate analogues have been evaluated against arthritis in animals, and there is no clear indication whether the antiarthritic properties of methotrexate are directly proportional to its cytotoxicity. Studies published in *Chem. Biol. Pteridines*, 847 (1986) DeGruyter, Berlin, N.Y. showed that adjuvant arthritis and streptococcal cell wall arthritis in rats responded to doses of methotrexate which were in good correlation to those used in man for treatment of rheumatoid arthritis and that timing and dosage were both important for reduction of inflammation. Both methotrexate and aminopterin were found to inhibit inflammation, but other antifolate compounds that did not possess a 2,4-diaminopyrimidine unit or a benzoylglutamate side chain were found ineffective.

U.S. Pat. No. 4,369,319, discloses 10-deazaaminopterin compounds possessing biological activity against leukemia as well as against other malignancies, including ascitic tumors in warm-blooded lower animals by the administration of 10-deazaaminopterin. The use of deazaaminopterin as antirheumaticum is described in the use patent 5,030,634. The sole compound described in the '634 patent is identical to the compound wherein both $R_1$ and $R_2$ are hydrogens described in U.S. Pat. No. 4,369,319.

Other derivatives of methotrexate, namely pyrido[2,3-]pyrimidines, disclosed in U.S. Pat. No. 5,026,851 were found to be active against neoplastic growth. The process to prepare these compounds is disclosed in the U.S. Pat. No. 4,988,813.

*J. Med. Chem.*, 29:1080–1087 (1986) describes a study indicating that modifications at the 5-and 10-positions of classical folic acid antimetabolites lead to compounds with favorable differential membrane transport in tumor versus normal proliferative tissue. *J. Heterocyclic Chem.*, 88:1 (1986), describes the synthesis of 5,10-dideazaaminopterin by two independent routes. *Cancer Research*, 49:5686–5691 (1988), describes studies examining a new class of 4-aminofolate analogues modified by an N to C conversion and alkyl substitution at the N-5 position of aminopterin and methotrexate.

*Chemistry and Biology of Pteridines*, (1989,) Walter de Gruyter & Co., Berlin, N.Y., discloses that modifications at the 5- and 10-positions of the classical antifolate structure have produced agents with antitumor activity superior to that of methotrexate. *J. Med. Chem.*, 83:678 (1990), reported the synthesis of the 10-methyl and 10-ethyl analogues of 5,10-dideazatetrahydrofolic acid (DDTHF), a potent inhibitor of glycinamide riboside (GAR) formyltransferase.

It is therefore a primary object of this invention to provide nontoxic but highly effective compounds for treatment of inflammatory diseases, such as rheumatoid arthritis, as well as an effective treatment and inhibition of malignant neoplasms of the blood forming tissues and effective inhibition of growth of malignant tumors with compounds which exhibit relatively low or no toxicity, compared to currently available drugs and treatments.

All references cited herein and in the following text are hereby incorporated by reference in their entirety.

SUMMARY

One aspect of the current invention are 5-alkyl and heteroaroyl-5-deazaaminopterin and 5,10-dideazaaminopterin compounds of formula (I)

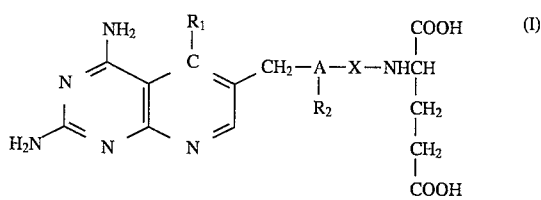

wherein A is CH or N;
wherein X is selected from

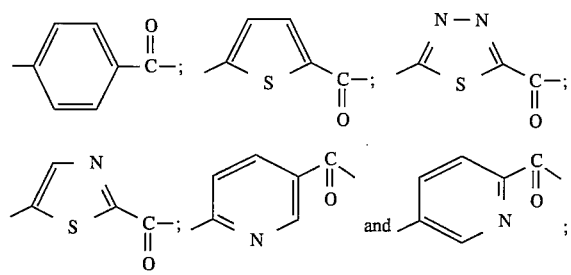

wherein $R_1$ is hydrogen or alkyl having from one to about eight carbon atoms, preferably from one to four carbon atoms;

and wherein $R_2$ is hydrogen, alkyl, alkenyl, or alkynyl having from one to about eight carbon atoms, preferably from one to four carbon atoms for alkyl and three to five carbon atoms for alkenyl and alkynyl.

Another aspect of the current invention is a method for treatment of rheumatoid arthritis by administering to a patient in need of such treatment an effective amount of the compound of formula (I) or its pharmaceutically acceptable salt.

Still another aspect of the current invention is a method for inhibition of malignant neoplastic growth of the blood forming tissue or malignant tumor growth of other tissues by administering to a patient in need of such treatment an effective amount of the compound of formula (I) or its pharmaceutically acceptable salt.

Another aspect of the current invention is a process for preparation of 10-deazaaminopterins and 5,10-dideazaaminopterins and 8,10-dideazaaminopterins starting from the corresponding homoterephthalic acid diester comprising steps:

(a) coupling the corresponding dicarboxylic acid diester having the formula

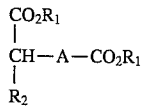

with the corresponding diaminopterin 6-methylene halide having the formula

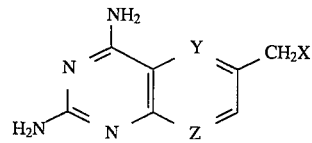

thereby forming a pteroic acid diester having the formula

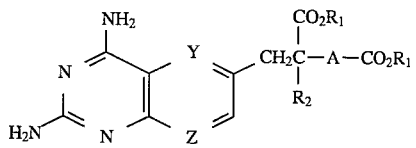

(b) hydrolysing the two ester groups of the pteroic acid diester to form the corresponding carboxylic acid groups; and

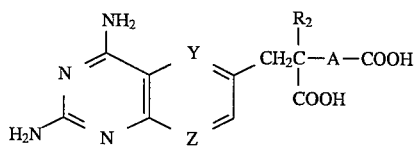

(c) monodecarboxylating the diacid, thereby removing the carboxylic acid group attached to the carbon alpha of the A group and forming a pteroic acid of the formula

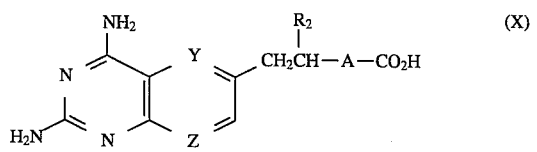

Still yet another aspect of the current invention is a process for preparation of 2,4-diamino-4-deoxy-10 deazapteric acids of formula (X)

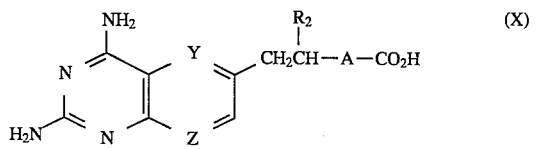

wherein A is CH;
wherein Z is N or CH;
wherein R is lower alkyl having from one to four carbon atoms;
wherein Y is N or $CHR_1$, wherein $R_1$ is hydrogen or alkyl having from one to about eight carbon atoms,
wherein $R_2$ is hydrogen or alkyl having from one to about eight carbon atoms, preferably from one to four carbon atoms, alkenyl, or alkynyl having from three to about eight carbon atoms, preferably from three to five carbon atoms for alkenyl and alkynyl;

said process comprising steps:

(a) reacting a 2,4 diamino-6-halomethylpterin with a carboxy aryl or heteroaroyl acetic acid diester in the presence of a base to form a 2,4-diamino-4-deoxy-10-carbalkoxy-10-deazapteroic acid ester;

(b) hydrolyzing said diester of step (a) with an aqueous base to form a 10-carboxy-2,4-diamino-10 -deazapteroic acid; and (c) decarboxylating the 10-carboxy-2,4-diamino-10 -deazapteroic acid by heating to form a 2,4-diamino-4-deoxy- 10-deazapteroic acid.

Still yet another aspect of this invention is a process for preparation of 10-deaza-2,4-diaminopteroic acids, 5,10-dideaza-2,4-diaminopteroic acids, 5-alkyl-5,10 -dideaza-2,4-diaminopteroic acids, 8,10-dideaza-2,4 -diaminopteroic acids.

DEFINITIONS

As used herein, the term "5-deazaaminopterin" includes the following compounds 5-deazaaminopterin, 5-alkyl-5 -deazaaminopterin, 5-deaza-heteroaroyl-aminopterin, 5-alkyl- 5-deaza-heteroaroyl-aminopterin, and all their analogues substituted with various $R_2$ substituents.

The term "5,10-dideazaaminopterin" includes the following compounds 5,10-dideazaaminopterin, 5-alkyl-5,10 -dideazaaminopterin, 5,10-dideaza-heteroaroyl-aminopterin, 5-alkyl-5,10-dideaza-heteroaroyl-aminopterin and all their analogues substituted with various $R_2$ substituents.

DETAILED DESCRIPTION OF THE INVENTION

The current invention concerns novel 5-alkyl and heteroaroyl-5-deazaaminopterin and 5,10-dideazaaminopterin compounds which are analogues of methotrexate. These compounds are exceptionally effective for treatment of rheumatoid arthritis or for inhibition of malignant neoplastic growth, particularly for treatment of leukemia.

The invention also provides a method of treating arthritis and other proliferative diseases, as well as a method for inhibition of malignant neoplastic growth. The method comprises administering to a human or other mammal having an inflammation of the joints or other evidence of the rheumatic disease or suffering from leukemia or tumorigenic growth, a therapeutically effective nontoxic amount of 5-alkyl, or heteroaroyl-5-deazaaminopterin and 5,10-dideazaaminopterin compound or a pharmaceutically acceptable salt thereof.

Additionally, the invention concerns a process for preparing 5-alkyl and heteroaroyl-5-deazaaminopterin and 5,10-dideazaaminopterin compounds from the appropriate corresponding homoterephthalic acid diester by coupling the diester with the corresponding diaminopterin halide thereby forming a pteroic acid diester, hydrolyzing the ester groups to form diacid, monodecarboxylating the diacid and forming a pteroic acid.

I. 5-deazaaminopterins and 5,10-dideazaaminopterins

A primary aspect of the present invention are 5-deazaaminopterin and 5,10-dideazaaminopterin compounds of the formula

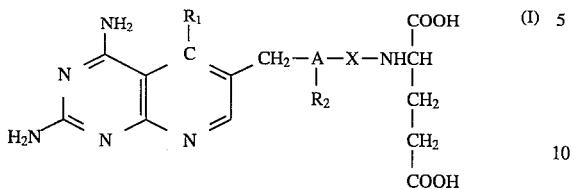

wherein A is CH or N;
wherein X is selected from

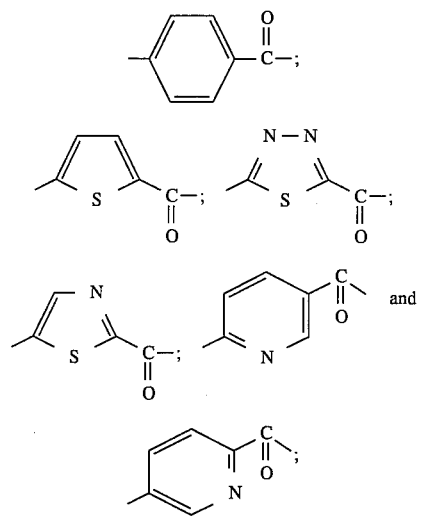

wherein $R_1$ is hydrogen or alkyl having from one to about eight carbon atoms, preferably from one to four carbon atoms;

and wherein $R_2$ is hydrogen, alkyl, alkenyl, or alkynyl having from one to about eight carbon atoms, preferably from one to four carbon atoms .for alkyl and three to five carbon atoms for alkenyl and alkynyl.

Exemplary alkyl substituent includes methyl, ethyl, propyl, iso-propyl, butyl, isobutyl, sec-butyl, tert-butyl, amyl, iso-amyl, sec-amyl, tert-amyl, hexyl, iso-hexyl, heptyl, iso-heptyl, octyl, iso-octyl, 2-ethyl hexyl, and tert-octyl.

Exemplary alkenyl substituent includes allyl, 1-propenyl, crotyl (2-butenyl), 2-pentenyl, 4-pentenyl, 2-hexenyl, 5-hexenyl, 3-isopropenyl, 3-isobutenyl, and 2-octenyl.

Exemplary alkynyl substituent includes propargyl, 2-butynyl, 3-butynyl, 2-pentynyl, 4-pentynyl, 2-hexynyl, and 2-octynyl.

A. 5-deazaaminopterin and 5,10-dideazaaminopterin compounds

One group of compounds according to the current invention are 5-alkyl 5-deazaaminopterins and 5,10-dideazaaminopterins of the formula

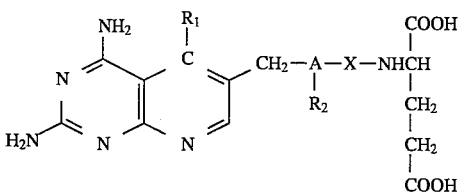

wherein A is N or CH, wherein X is

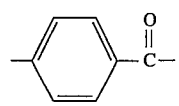

wherein $R_1$ is hydrogen or alkyl having from one to about eight carbon atoms, preferably from one to four carbon atoms;

and wherein $R_2$ is hydrogen, alkyl, alkenyl, or alkynyl having from one to about eight carbon atoms, preferably from one to four carbon atoms for alkyl and three to five carbon atoms for alkenyl and alkynyl.

The most preferred embodiment of the current invention is a subclass of 5-alkyl-5-deazaaminopterin compounds wherein A is N, wherein X is benzoyl, $R_1$ is hydrogen or alkyl having one to eight, preferably one to four, carbon atoms, and $R_2$ is hydrogen, alkyl from one to eight carbon atoms, and alkenyl or alkynyl having from three to about eight carbon atoms, preferably from three to about five carbon atoms. These compounds are exceptionally effective in the treatment of arthritis. These compounds are therefore especially preferred.

This subclass of compounds within the invention is defined by the formula II

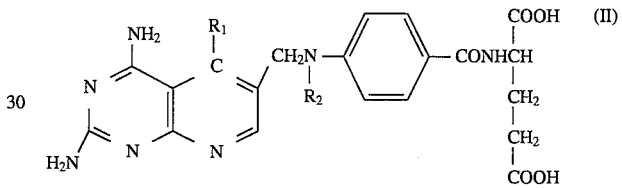

wherein $R_1$ is hydrogen or alkyl having from one to eight, preferably from one to four, carbon atoms, and $R_2$ is alkyl, alkenyl, or alkynyl having from one to about eight, preferably from one to three carbon atoms for alkyl, and three to five, carbon atoms for alkenyl and alkynyl.

Another preferred embodiment of the current invention is a subclass of compounds within the invention wherein A is CH, wherein X is benzoyl and $R_1$ is hydrogen or alkyl having from one to eight, preferably from one to four, carbon atoms, and $R_2$ is alkyl, alkenyl or alkynyl having from three to about eight carbon atoms, preferably from three to about five carbon atoms. These compounds are novel and are effective in the treatment of arthritis, leukemia and tumors.

This subclass of compounds within the invention accordingly is defined by the formula III

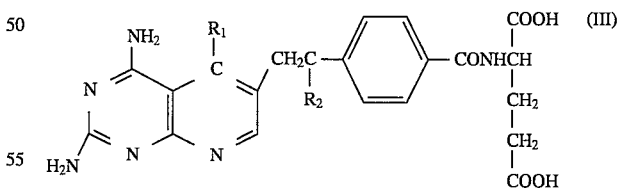

wherein $R_1$ is hydrogen or alkyl having from one to eight, preferably from one to four, carbon atoms, and $R_2$ is alkyl, alkenyl, or alkynyl having from three to about eight, preferably from three to five, carbon atoms.

Exemplary 5-alkyl-5-deazaaminopterin and 5,10-dideazaaminopterin compounds falling within formulae I, II, or III are shown in the following Table 1.

In Table 1 the substituent A can be either CH or N. Substituent X is benzoyl. Substituents $R_1$ and $R_2$ are as shown in Table 1. Preparation of compounds listed in Table 1 where $R_1$ is hydrogen, or alkyl and A is N is illustrated in Reaction Scheme 1 and in Examples 1 and 2. Preparation of compounds listed in Table 1 where $R_1$ is hydrogen or alkyl and A is CH is illustrated in Scheme 2 and in Example 14.

TABLE 1

Deazaaminopterin Compounds
Series a = A is N
Series b = A is CH

| Compound No. | $R_1$ | $R_2$ | X |
|---|---|---|---|
| 1 a, b | H | H | |
| 2 a, b | H | $CH_3$ | 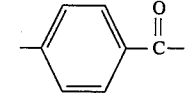 |
| 3 a, b | H | $C_2H_5$ | |
| 4 a, b | H | $C_3H_7$ | |
| 5 a, b | H | $CH_2=CHCH_2-$ | |
| 6 a, b | H | $CH\equiv CCH_2-$ | |
| 7 a, b | H | $C_5H_{11}$ | |
| 8 a, b | H | $C_8H_{17}$ | |
| 9 a, b | $CH_3$ | H | |
| 10 a, b | $CH_3$ | $CH_3$ | |
| 11 a, b | $CH_3$ | $C_2H_5$ | |
| 12 a, b | $CH_3$ | $C_3H_7$ | |
| 13 a, b | $CH_3$ | $CH_2=CHCH_3$ | |
| 14 a, b | $CH_3$ | $CH\equiv CCH_2$ | |
| 15 a, b | $CH_3$ | $C_8H_{17}$ | |
| 16 a, b | $C_2H_5$ | H | |
| 17 a, b | $C_2H_5$ | $CH_3$ | |
| 18 a, b | $C_2H_5$ | $C_2H_5$ | |
| 19 a, b | $C_2H_5$ | $CH_2=CHCH_2$ | |
| 20 a, b | $C_2H_5$ | $CH\equiv CCH_2$ | |
| 21 a, b | $C_3H_7$ | H | |
| 22 a, b | $C_3H_7$ | $CH_3$ | |
| 23 a, b | i-$C_3H_7$ | H | |
| 24 a, b | i-$C_3H_7$ | $CH_3$ | |
| 25 a, b | n-$C_4H_9$ | H | |
| 26 a, b | n-$C_4H_9$ | $CH_3$ | |
| 27 a, b | $C_5H_{11}$ | H | |
| 28 a, b | $C_8H_{17}$ | H | |

B. Heteroaroyl 5-deazaaminopterin and 5,10-dideazaminopterin compounds

Another group of compounds according to the current invention are heteroaroyl 5-deazaaminopterins and 5,10-dideazaminopterins of formula

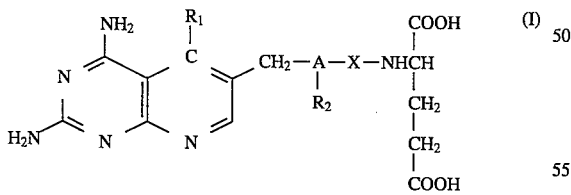 (I)

wherein A is N or CH;
wherein X is selected from

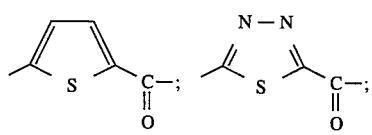

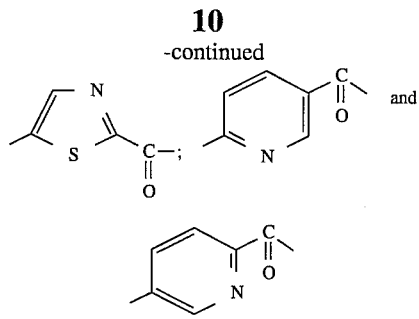

wherein $R_1$ is hydrogen or alkyl having from one to about eight, preferably from one to three, carbon atoms;
and $R_2$ is hydrogen or alkyl, alkenyl, or alkynyl having from one to about eight, preferably from one to about three, carbon atoms for alkyl and three to five carbon atoms for alkenyl and alkynyl.

Within this group, one subclass of preferred compounds are those where X is thienyl and thienyl analogues of the formula

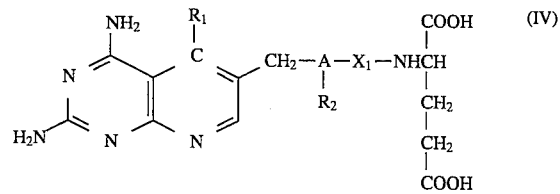 (IV)

wherein A is N or CH;
wherein $X_1$ is selected from the group consisting of

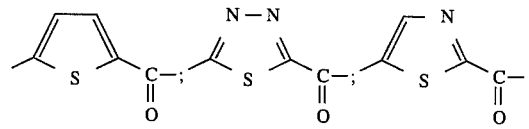

and $R_1$ is hydrogen or alkyl having from one to about eight, preferably from one to three carbon atoms;
and $R_2$ is hydrogen or alkyl, alkenyl, or alkynyl having for one to about eight, preferably from one to three, carbon atoms for alkyl and three to five carbon atoms for alkenyl and alkynyl.

Another preferred subclass of heteroaroyl compounds are of the formula

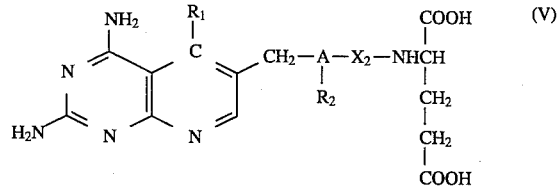 (V)

wherein A is CH;
$X_2$ is selected from the group consisting of

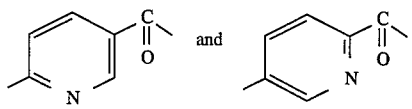

and $R_1$ is hydrogen or alkyl having from one to about eight, preferably from one to three, carbon atoms;
and $R_2$ is hydrogen or alkyl, alkenyl, or alkynyl having from one to about eight, preferably from one to three, carbon atoms for alkyl and three to five carbon atoms for alkenyl and alkynyl.

Exemplary heteroaroyl deazaaminopterin compounds falling within formula IV or V are shown in the following Tables 2 and 3.

Table 2 lists compounds where the substituent A is N, substituent X is heteroaroyl, and substituents $R_1$ and $R_2$ are as shown in Table 2. Preparation of compounds listed in Table 2 is illustrated in Reaction Scheme 3 and Examples 3–7.

TABLE 2

5-Deazaaminopterin Compounds (A = N)

| Compound No. | $R_1$ | $R_2$ | X |
|---|---|---|---|
| 29 | H | H | |
| 30 | H | $CH_3$ | thiophene-C(=O)– |
| 31 | H | $C_2H_5$ | |
| 32 | H | $C_3H_7$ | |
| 33 | H | i-$C_3H_7$ | |
| 34 | H | $C_4H_9$ | |
| 35 | H | $C_5H_{11}$ | |
| 36 | H | $C_8H_{17}$ | |
| 37 | H | $CH_2=CHCH_2-$ | |
| 38 | H | $HC\equiv CCH_2-$ | |
| 39 | $CH_3$ | H | |
| 40 | $CH_3$ | $CH_3$ | |
| 41 | $CH_3$ | $C_2H_5$ | thiophene-C(=O)– |
| 42 | $CH_3$ | $C_3H_7$ | |
| 43 | $CH_3$ | i-$C_3H_7$ | |
| 44 | $CH_3$ | $CH_2=CH_2CH_2-$ | |
| 45 | $CH_3$ | $HC\equiv CCH_2-$ | |
| 46 | $C_2H_5$ | H | |
| 47 | $C_2H_5$ | $CH_3$ | |
| 48 | $C_2H_5$ | $C_2H_5$ | |
| 49 | $C_3H_7$ | H | |
| 50 | $C_3H_7$ | $CH_3$ | |
| 51 | H | H | |
| 52 | H | $CH_3$ | thiazole-C(=O)– |
| 53 | H | $C_3H_7$ | |
| 54 | H | $C_4H_9$ | |
| 55 | H | $CH_2=CHCH_2-$ | |
| 56 | H | $HC\equiv CHCH_2-$ | |
| 57 | $CH_3$ | H | |
| 58 | $CH_3$ | $C_2H_5$ | |
| 59 | $CH_3$ | $C_5H_{11}$ | |
| 60 | $C_2H_5$ | H | |
| 61 | $C_2H_5$ | $CH_3$ | |
| 62 | $C_3H_7$ | H | |
| 63 | H | H | |
| 64 | H | $CH_3$ | thiadiazole-C(=O)– |
| 65 | H | $C_3H_7$ | |
| 66 | H | $C_4H_9$ | |
| 67 | H | $CH_2=CHCH_2-$ | |
| 68 | H | $HC\equiv CHCH_2-$ | |
| 69 | $CH_3$ | H | |
| 70 | $CH_3$ | $C_2H_5$ | |
| 71 | $CH_3$ | $C_5H_{11}$ | |
| 72 | $C_2H_5$ | H | |
| 73 | $C_2H_5$ | $CH_3$ | |
| 74 | $C_3H_7$ | H | |

Preparations of Compounds 29–30 (Table 2) is illustrated in Example 3. Preparation of compound 39 is illustrated in Example 2. Preparation of compounds 40–45 is illustrated in Examples 4 and 5. Preparation of compounds 46–48 is illustrated in Example 6. Preparation of compounds 49–50 is illustrated in Example 7.

In compounds shown in Table 3, the substituent A is CH, substituent X is heteroaroyl and substituents $R_1$ and $R_2$ are shown in Table 3. Preparation of compounds listed in Table 3 is illustrated in Reaction Schemes 4–5 and in Examples 8–10.

TABLE 3

Deazaaminopterin Compounds (A = CH)

| Compound No. | $R_1$ | $R_2$ | X |
|---|---|---|---|
| 75 | H | H | |
| 76 | H | $CH_3$ | |
| 77 | H | $C_2H_5$ | |
| 78 | H | $C_3H_7$ | thiophene-C(=O)– |
| 79 | H | i-$C_3H_7$ | |
| 80 | H | $C_4H_9$ | |
| 81 | H | $C_5H_{11}$ | |
| 82 | H | $C_8H_{17}$ | |
| 83 | H | $CH_2=CHCH_2-$ | |
| 84 | H | $HC\equiv CCH_2-$ | |
| 85 | $CH_3$ | H | |
| 86 | $CH_3$ | $CH_3$ | |
| 87 | $CH_3$ | $C_2H_5$ | |
| 88 | $CH_3$ | $C_3H_7$ | |
| 89 | $CH_3$ | i-$C_3H_7$ | |
| 90 | $CH_3$ | $CH_2=CH_2CH_2-$ | |
| 91 | $CH_3$ | $HC\equiv CCH_2-$ | |
| 92 | $C_2H_5$ | H | |
| 93 | $C_2H_5$ | $CH_3$ | |
| 94 | $C_2H_5$ | $C_2H_5$ | |
| 95 | $C_3H_7$ | H | |
| 96 | $C_3H_7$ | $CH_3$ | |
| 97 | H | H | |
| 98 | H | $CH_3$ | |
| 99 | H | $C_3H_7$ | |
| 100 | H | $C_4H_9$ | pyridine-C(=O)– |
| 101 | H | $CH_2=CHCH_2-$ | |
| 102 | H | $HC\equiv CHCH_2-$ | |
| 103 | $CH_3$ | H | |

TABLE 3-continued

Deazaaminopterin Compounds (A = CH)

| Compound No. | $R_1$ | $R_2$ | X |
|---|---|---|---|
| 104 | $CH_3$ | $C_2H_5$ | |
| 105 | $CH_3$ | $C_5H_{11}$ | |
| 106 | $C_2H_5$ | H | |
| 107 | $C_2H_5$ | $CH_3$ | |
| 108 | $C_3H_7$ | H | |
| 109 | H | H | |
| 110 | H | $CH_3$ | |
| 111 | H | $C_3H_7$ | ![p-benzoyl]  |
| 112 | H | $C_4H_9$ | |
| 113 | H | $CH_2=CHCH_2-$ | |
| 114 | H | $HC\equiv CHCH_2-$ | |
| 115 | $CH_3$ | H | |
| 116 | $CH_3$ | $C_2H_5$ | |
| 117 | $CH_3$ | $C_5H_{11}$ | |
| 118 | $C_2H_5$ | H | |
| 119 | $C_2H_5$ | $CH_3$ | |
| 120 | $C_3H_7$ | H | |
| 121 | H | H | |
| 122 | H | $CH_3$ | |
| 123 | H | $C_3H_7$ | [thiazole-C(=O)-] |
| 124 | H | $C_4H_9$ | |
| 125 | H | $CH_2=CHCH_2-$ | |
| 126 | H | $HC\equiv CHCH_2-$ | |
| 127 | $CH_3$ | H | |
| 128 | $CH_3$ | $C_2H_5$ | |
| 129 | $CH_3$ | $C_5H_{11}$ | |
| 130 | $C_2H_5$ | H | |
| 131 | $C_2H_5$ | $CH_3$ | |
| 132 | $C_3H_7$ | H | |
| 133 | H | H | |
| 134 | H | $CH_3$ | |
| 135 | H | $C_3H_7$ | [thiadiazole-C(=O)-] |
| 136 | H | $C_4H_9$ | |
| 137 | H | $CH_2=CHCH_2-$ | |
| 138 | H | $HC\equiv CHCH_2-$ | |
| 139 | $CH_3$ | H | |
| 140 | $CH_3$ | $C_2H_5$ | |
| 141 | $CH_3$ | $C_5H_{11}$ | |
| 142 | $C_2H_5$ | H | |
| 143 | $C_2H_5$ | $CH_3$ | |
| 144 | $C_3H_7$ | H | |

In compounds shown in Table 3, substituent A is CH, substituent X is heteroaroyl, substituents $R_1$ and $R_2$ are as seen in Table 3. Preparation of compounds 75–96 is shown in Example 8. Preparation of compounds 97–108 is shown in Examples 9 and 10. Preparation of compounds 109–144 is according to methods generally described in Examples 8–10.

II. Preparation of -5-deazaaminopterin and 5,10-dideazaaminopterin compounds 5-deazaaminopterins and 5,10-dideazaaminopterins are prepared by procedures described in following Reaction Schemes 1–5 or, in alternative, they can be prepared by the processes described in Section III.

The Examples 1–17 illustrate application of procedures illustrated in Reaction Schemes 1–5 to the preparation of specific compounds 1–144. Reference numbers within the Examples refer to compounds or their precursors and intermediates as described in steps of Reaction Schemes and to compounds listed in Tables 1–3.

Reaction Scheme 1 illustrates preparation and synthesis of the compounds of formula II, wherein A is N and X is benzoyl, by the modified method described in *J. Med. Chem.*, 29, 1080–087 (1986), incorporated herein by reference.

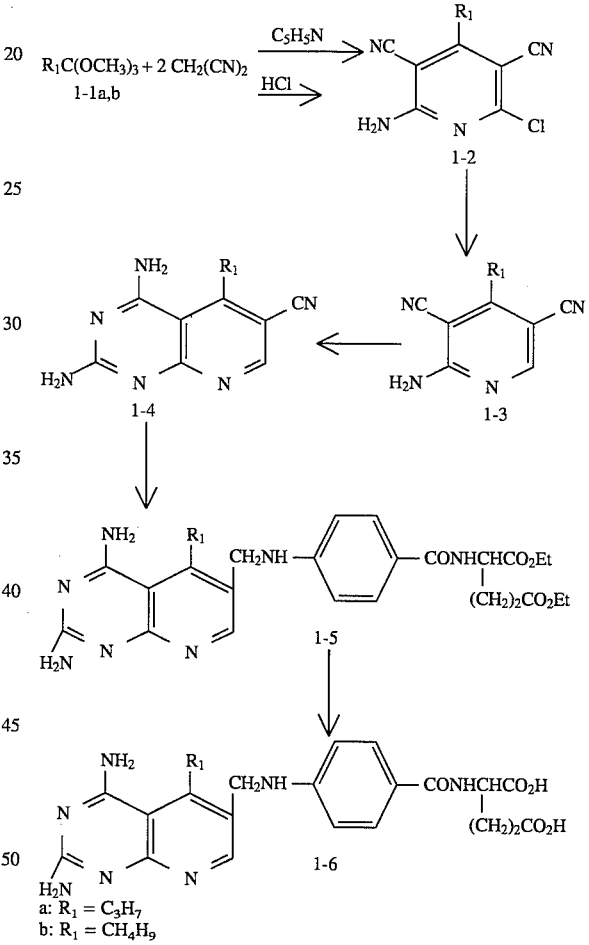

Reaction Scheme 1

Reaction Scheme 1 illustrates a preparation of 5-alkyl-5-deazaaminopterins wherein A is N, X is benzoyl, wherein $R_1$ is either propyl (compound a) or butyl (compound b). Using the starting compound, having the different $R_1$ substituents, other compounds may be prepared using the same process.

Typically, these compounds are prepared by cyclization of the starting orthoester I-1, such as trimethylorthobutyrate ($R_1$ is $C_3H_7$) or trimethylorthovalerate ($R_1$ is $C_4H_9$) with malononitrile in the presence of an acid to obtain a 2-amino-3,5-dicyano-4-alkyl-6-chloropyrimidine (I-2). Compound I-2 is converted into compound I-3, a 2-amino-4-alkyl-3,5-pyridinedicarbonitrile, by hydrogenolysis over a catalyst such as palladium chloride, in the presence of an organic solvent, such as dimethyl formamide. Compound I-4, a 2,4-diamino-5-alkylpyrido[2,3-d]pyrimidine-6-carbonitrile, is obtained by an annulation reaction of compound I-3 with anhydrous guanidine, preferably anhydrous guanidine HCl, in the presence of a base, such as sodium methoxide, at temperatures about 130°–180° C., preferably about 150°–160° C. under constant stirring for about 5–15 hours. Compound I-4 is submitted to reductive condensation with a dialkyl, preferably with diethyl-N-(4-amino-benzoyl)-L-glutamate in a solvent, preferably acetic acid containing a nickel catalyst, such as Raney nickel. The mixture is kept under hydrogen until hydrogen absorption ceases. The catalyst is removed and the product is isolated. Purified product I-5 a dialkyl N-[4-[(2,4-diamino-5-alkylpyrido[2,3-d]pyrimidine-6-yl)methyl]amino]benzoyl-L-glutamate, is dissolved in an alcohol, preferably methanol, and treated with a base, preferably sodium hydroxide. The reaction mixture is kept at a temperature between 18–27° C., preferably around 22° C., for about 3 days or longer until the conversion of the precursor I-5 to the 5-deazaaminopterin (I-6), wherein A is N and X is benzoyl, is complete.

All compounds where the substituent $R_1$ is alkyl, are prepared by the procedure illustrated in the Reaction Scheme 1, by using an appropriately substituted $R_1$ in compound I-1. The method of their preparation is illustrated in Examples 1 and 2.

Reaction Scheme 2

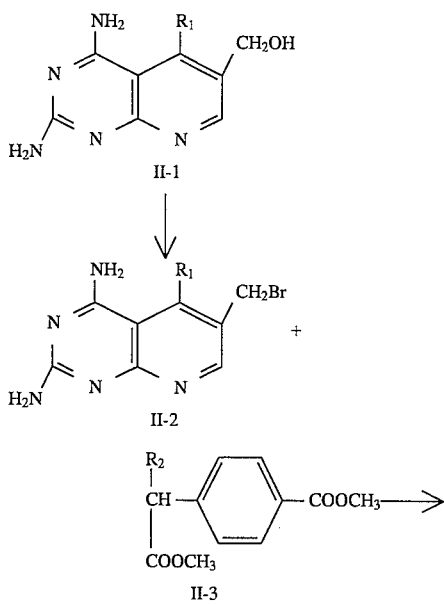

-continued
Reaction Scheme 2

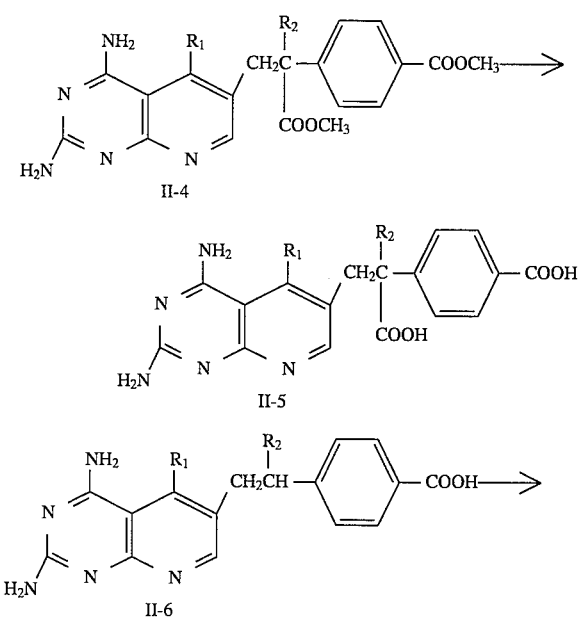

$R_1$ = H, alkyl
$R_2$ = H, alkyl, alkenyl, alkynyl

Reaction Scheme 2 illustrates the preparation of 5-alkyl-5-deazaaminopterins wherein A is CH, X is benzoyl, $R_1$ is hydrogen or alkyl and $R_2$ is hydrogen, alkyl, alkenyl or alkynyl.

The synthesis of these compounds begins with bromination of the starting compound II-1, namely 2,4-diaminopyrido-[2,3-d]pyrimidine-6-methanol. The compound II-1 is brominated by using essentially the procedure described in *J. Med. Chem*, 35:332 (1992) yielding 6-(bromomethyl)-2,4-diaminopyrido [2,3-d]pyrimidine (II-2). Compound II-2 is reacted with appropriately $R_2$ substituted homoterephthalate diester (L I-3) to yield compound II-4, namely a 10-alkoxycarbonyl 2,4-diamino-5,10-dideazapteroic acid ester. Compound II-4 is hydrolyzed with mild base to yield II-5, namely a 10-carboxy 2-4-diamino-5,10-dideazapteroic acid, which in turn is heated in a suitable solvent to yield a 5,10-dideazaaminopteroic acid II-6.

The synthesis of compounds of formula I and IV wherein A is N and X is any of the heterocyclic rings set out for these formula IV is carried out by the procedure seen in Reaction Scheme 3.

Reaction Scheme 3

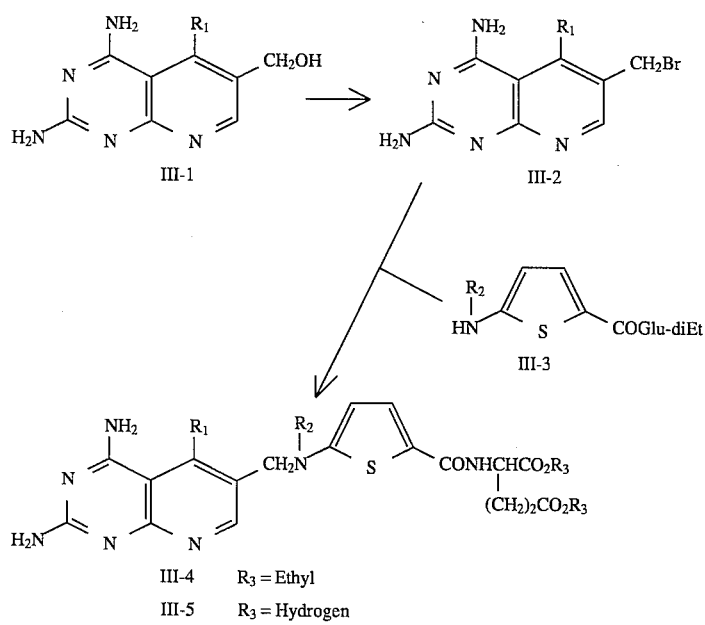

wherein $R_1$ is hydrogen or alkyl, $R_2$ is hydrogen, alkyl, alkenyl or alkynyl and $R_3$ is hydrogen or alkyl.

Specifically, in compound III-4, $R_3$ is ethyl and in compound III-5, $R_3$ is hydrogen.

For series of compounds prepared, in the compound:

(a) $R_1$ is hydrogen and $R_2$ is hydrogen;

(b) $R_1$ is methyl and $R_2$ is hydrogen;

(c) $R_1$ is methyl and $R_2$ is methyl;

(d) $R_1$ is ethyl and $R_2$ is methyl;

(e) $R_1$ is propyl and $R_2$ is hydrogen.

Reaction Scheme 3 illustrates the preparation of compounds wherein X is a heteroaryl such as thiophene, A is N, and $R_1$, $R_2$, and $R_3$ are as listed above and in Table 2.

The reaction begins with bromination of the starting methanol compound 2,4-diaminopyrido-[2,3-d]pyrimidine-6-methanol III-1 using the procedure described in *J. Med. Chem.*, 35:332 (1992) to yield 6-(bromomethyl)-2,4-diaminopyrido [2,3-d]pyrimidine (III-2). 6-(Bromomethyl)- 2,4-diaminopyrido[2,3-d]pyrimidine III-2 is reacted with a heteroaroyl ester containing compound such as N-(5-aminothiophene-2-carbonyl)-L-glutamic acid diethyl ester (III-3) to provide the heteroaroyl-5-deazaaminopterin diethylester (III-4), which yields compound III-5, wherein the $R_3$ is hydrogen, by reaction with a mild base such as dilute sodium hydroxide.

Reaction Scheme 4 illustrates the preparation of thiophene analogues of formula I where A is CH. These compounds are illustrated in Example 8.

Reaction Scheme 4

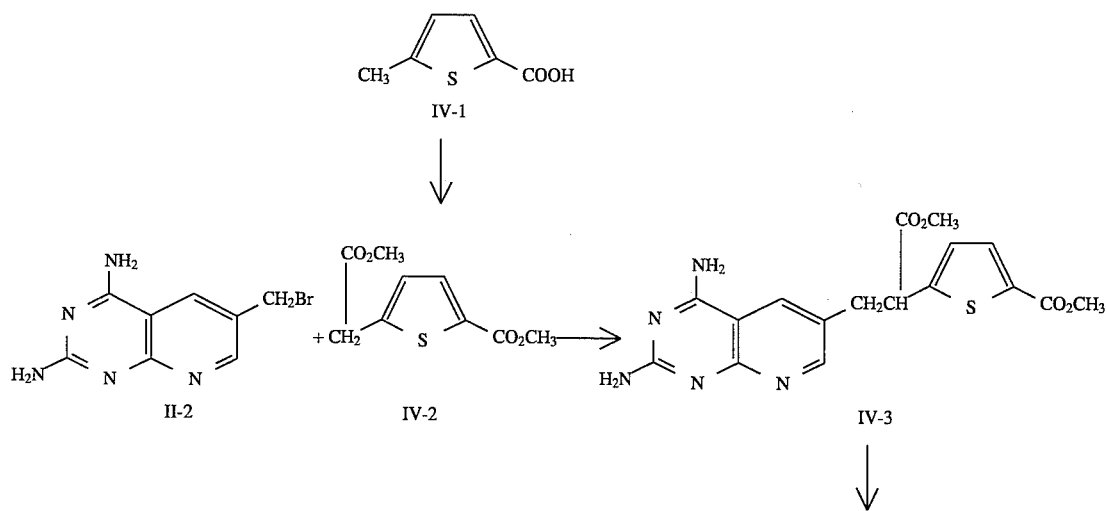

-continued
Reaction Scheme 4

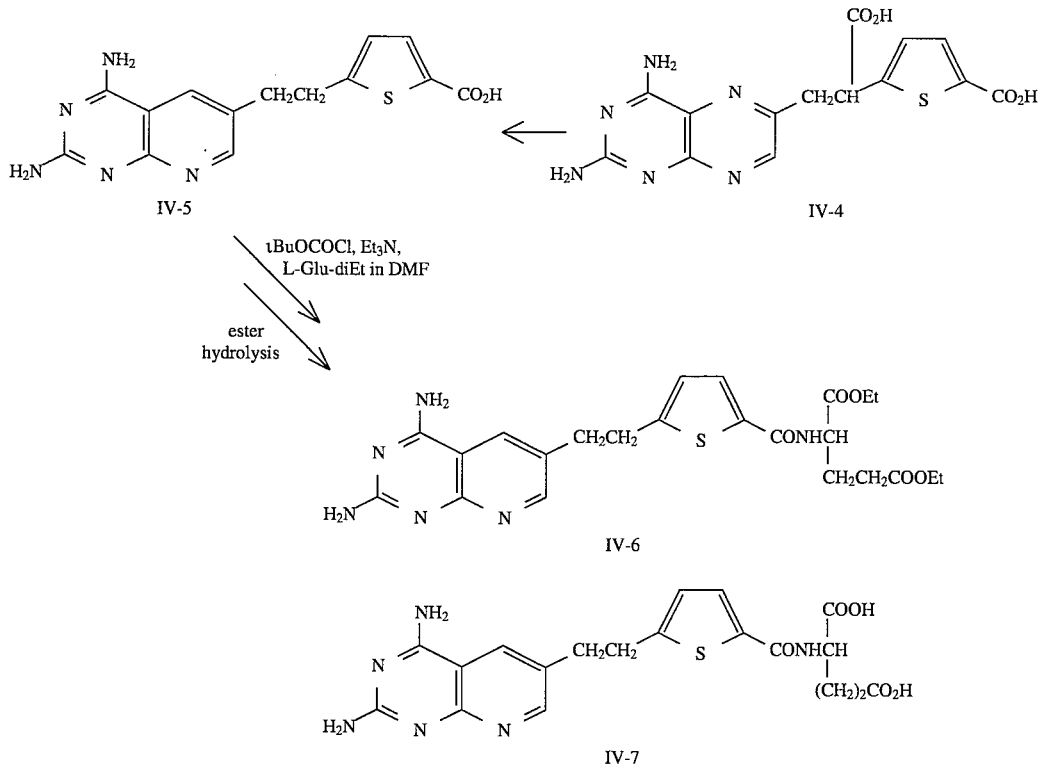

Compounds prepared by procedure of the Reaction Scheme 4 are generally prepared from the corresponding thiophene carboxylic acid compound IV-1. The dianion of compound IV-1 is prepared by treatment of compound IV-1 with 2 equivalents of lithium diisopropyl amide in a solvent such as tetrahydrofuran and carbonated with carbon dioxide to afford the dilithio salt 5-carboxythiophene-2-acetic acid. Esterification of the crude salt mixture with dry HCl, or other strong acid, in methanol gives the 2'-carboxythiophene-5-acetic acid diester (IV-2). The anion of compound IV-2, as obtained by treatment with sodium hydride in dimethyl formamide, is reacted with 6-(bromomethyl)-2,4-diaminopyrido[2,3-d]pyrimidine, compound II-2, in dimethylformamide at temperatures between −10° to −30° C., to provide the diester (IV-3). The diester IV-3 is hydrolyzed with a base, such as sodium hydroxide, to provide the dicarboxylic acid compound (IV-4). Compound IV-4 is readily converted to the mono acid IV-5 by dissolving IV-4 in DMSO and heating the solution to about 120° C. to provide compound IV-5. Compound IV-5 is coupled with diethyl glutamate, preferably by the mixed anhydride procedure using triethylamine-isobutyl chloroformate to afford the pteroyl glutamate diester IV-6. Compound IV-6 is then converted to appropriate glutamic acid compound IV-7 by hydrolysis with a base, such as sodium hydroxide, in the presence of a lower alcohol, such as methanol, ethanol, propanol or butanol.

Reaction Scheme 5 illustrates the preparation compounds of formula I wherein X is 2-pyridyl, A is CH and $R_1$ is hydrogen or lower alkyl.

Reaction Scheme 5

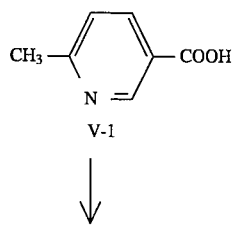

-continued
Reaction Scheme 5

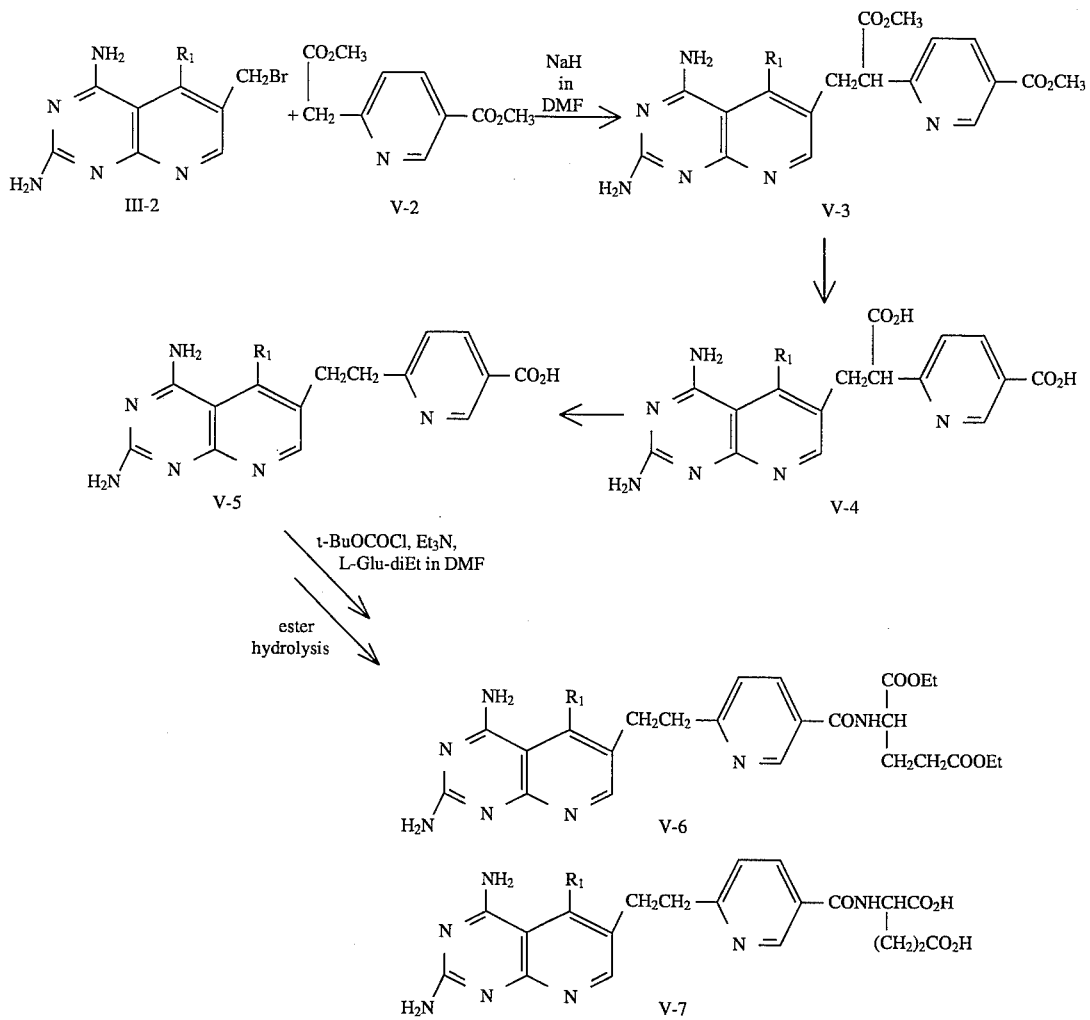

Heteroaroyl-5,10-diazaaminopterins of formula I wherein the moiety X is 2-pyridyl are prepared essentially by a process similar to that described above for the thiophene analogs.

The synthesis of the 2-pyridyl analogs is shown in Scheme 5 and represented by Examples 9 and 10. The dimethyl ester compound V-2 is prepared similarly to compound IV-2 from methylnicotinic acid V-1. Dimethyl ester V-2 is alkylated with compound III-2 to produce compound V-3, 10-carboxy-5,10-dideaza-3-azapteroic acid diester which, in turn, is hydrolyzed to produce 10-carboxy-5,10-dideaza-3-azapteroic acid V-4. Compound V-4 is converted to compound V-5 by suspending the compound V-4 in an organic solvent such as dimethylformamide, and the mixture is heated under constant stirring at about 55°–85° C., preferably at about 75° C. for 5–60 minutes, preferably for about 20 minutes. After the evolution of $CO_2$ ceases, the solvent is removed in vacuo yielding compound V-5. Compound V-5 is coupled with diethyl L-glutamate, as described in Reaction Scheme 4, to yield the ester V-6 which is hydrolyzed to produce the L-glutamic acid derivative V-7.

Other variations of pyridyl or other heterocycles represented in Formula I are prepared in a similar manner, including modifications which may be necessary depending on the target product, as shown in Schemes 4 and 5, and as represented by Examples 8–10.

Synthesis of 8,10-dideazaaminopterin compounds has also been accomplished by the process of the present invention as outlined in Reaction Scheme 6.

Reaction Scheme 6

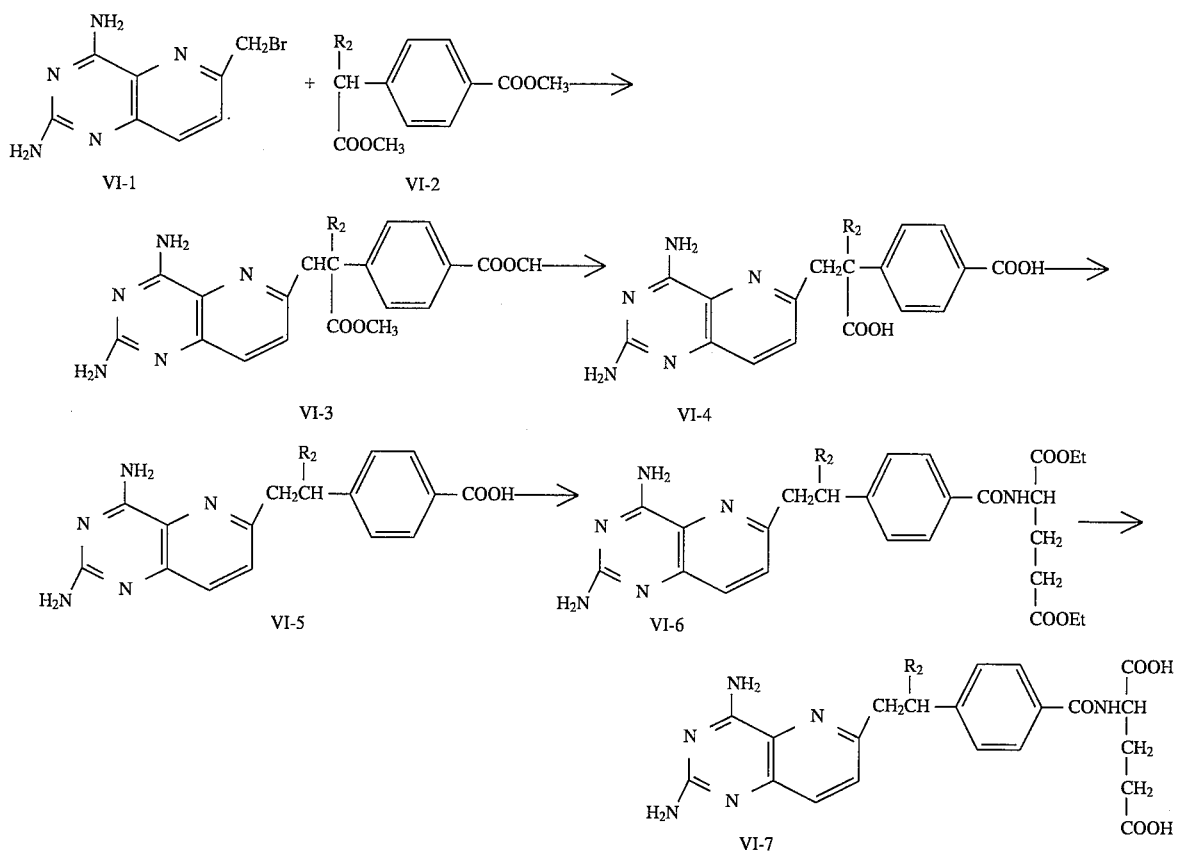

$R_2$ = H, alkyl, alkenyl, alkynyl

III. Process for Preparation of 5-Deazaaminopterins and 5,10-Dideazaaminopterins 10-Deazaaminopterin compounds of the current invention are generally prepared by a process comprising initial steps:

(a) coupling the corresponding homoterephthalic dicarboxylic acid diester having the formula

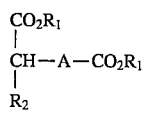

with the corresponding diaminopterin 6-methylene halide having the formula

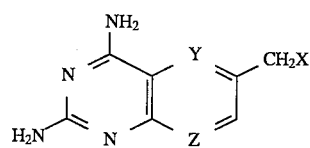

thereby forming a pteroic acid diester having the formula

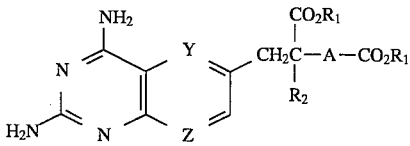

(b) hydrolysing the two ester groups of the pteroic acid diester to form the corresponding dicarboxylic acid groups; and

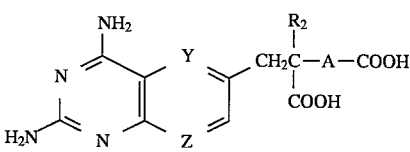

(c) monodecarboxylating the diacid, thereby removing the carboxylic acid group attached to the carbon alpha of the A group and forming a pteroic acid of the formula

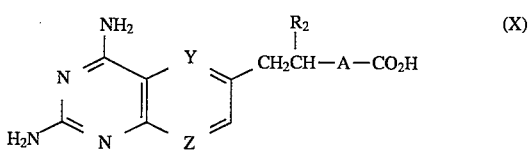
(X)

Resulting pteroic acid is then converted to its corresponding 5-deazaaminopterin or 5,10-dideazaamino pterin.

In alternative, compounds 2,4-diamino-4-deoxy-10 deazapteric acids of formula (X)

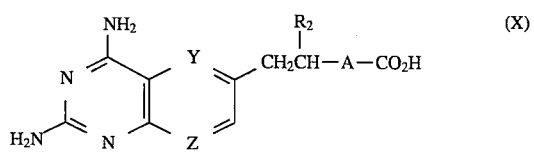

wherein A is CH;
wherein X is N or CH;
wherein Y is N or R, wherein R is hydrogen or alkyl having from one to about eight carbon atoms;
by a process comprising steps:

(a) reacting 2,4 diamino-6-halomethylpteridin or 5 -deazapterin with carboxy aryl or heteroaroyl acetic acid diester in the presence of a base to form 2,4-diamino-4 -deoxy-10-carbalkoxy-10-deazapteroic acid ester;

(b) hydrolyzing said diester of step (a) with an aqueous base to form 10-carboxydiamino-10-deazapteroic acid; and (c) dexarboxylating the 10-carboxydiamino-10 -deazapteroic acid by heating to form 2,4-diamino-4-deoxy-10-deazopteroic acid.

The synthesis of compounds of formulae I-V wherein A is CH and X is any of the heterocyclic rings set out for these formulae can be carried out by Reaction Scheme 7 which follows.

A is selected from the group consisting of aryl and heteroaryl having from two to about twenty carbon atoms and up to three hetero atoms selected from nitrogen, oxygen, and sulfur.

For series illustrative of compounds prepared by Reaction Scheme 7, in the compound VII 5a–e:

a) Y and Z are nitrogen, $R_2$ is allyl, A is 4-phenyl;

b) Y and Z are nitrogen, $R_2$ is propargyl, A is 4-phenyl;

c) Y is CH, Z is nitrogen, $R_2$ is hydrogen, A is 4-phenyl;

d) Y and Z are nitrogen, $R_2$ is hydrogen, A is 2,5-thiophene;

e) Y is nitrogen, Z is CH, $R_2$ is methyl, A is 4-phenyl.

Typically, in the process for production of 10 -deazaminopterins, 8, 10-dideazaminopterins and 5,10 -dideazaminopterins, the 6-methylene halide of the selected pterin or deazapterin nucleus VII-1 is coupled with the selected diester VII-2 having the desired A group via the mono anion as formed with alkali metal hydrides such as NaH or KH in an inert polar solvent such as dimethyl sulfoxide, dimethyl formamide, N-methyl pyrrolidone, glycol ethers or tetrahydrofuran. Alkali metal hydroxides, such as sodium hydroxide and potassium hydroxide, and alkali metal alkoxides, such as sodium or potassium alkoxides can be substituted for the alkali metal hydride.

The coupling proceeds at low temperatures between –30° to 25° C.; there is no critical lower limit, except that the reaction mixture should remain fluid at the reaction temperature. The temperature should not usually exceed room temperature, such as 25° C. to minimize side reactions and decomposition of reaction products.

Reaction Scheme 7

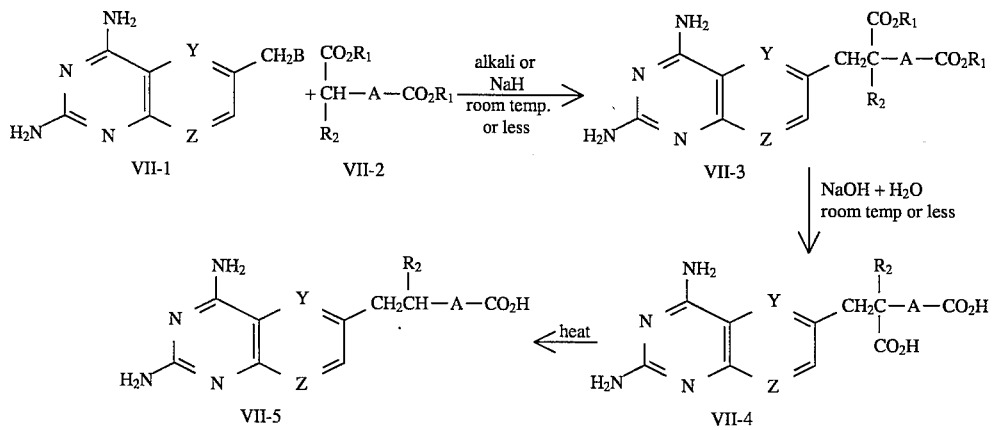

Series a. Y = Z = N, $R_2$ = allyl, A = 4-phenyl
b. Y = Z = N, $R_2$ = prgl, A = 4-phenyl
c. Y = CH, Z = N, $R_2$ = H, A = 4-phenyl
d. Y = Z = N, $R_2$ = H, A = 2,5-thiophene
e. Y = N, Z = CH, $R_2$ = $CH_3$, A = 4-phenyl wherein
B is halogen, such as chlorine, bromine or iodine:

Y is selected from the group consisting of N or $CR_3$ where $R_3$ is hydrogen or, alkyl of from one to about eight carbon atoms;

Z is N or CH;

$R_1$ is selected from the group consisting of alkyl, cycloalkyl, and alkaryl having from one to about twelve carbon atoms;

$R_2$ is selected from the group consisting of alkyl, alkenyl, alkynyl, having from one to about twenty carbon atoms; and In general, the $R_2$ substituent may be introduced via alkylation of the mono anion of dimethyl homoterephthalate with an appropriate alkyl halide. Alternatively, an appropriate p-alkyl benzoic acid (e.g., p-ethylbenzoic) or alkylheterocyclic acid (e.g., 5-ethyl-2-thenoic acid or 6 -ethylnicotinic acid) may be converted to its dianion via treatment with lithium diisopropyl amide, carbonated with $CO_2$ and esterified to afford the desired substrate for alkylation by an appropriate 2,4-diamino-6 -bromomethylpterin or deazapterin.

The diester of the pteroic acid VII-3 is then hydrolyzed to the corresponding diacid VII-4 by alkali metal hydroxide in aqueous or aqueous/alcoholic medium, also at a temperature below about 25° C., preferably at room temperature. The hydrolyzed reaction product is then precipitated by addition of an acid such as hydrochloric, sulfuric or acetic acid to a pH within the range from about 4 to about 6.5, preferably from 5 to 6 to avoid formation of the amine salt, which might interfere with the next step, monodecarboxylation of the diacid VII-4 to the monoacid VII-5.

The monodecarboxylation is carried out at an elevated temperature at which the reaction proceeds, but below that at which decomposition of reaction product occurs. Usually, temperatures within the range from about 100° C. to about 150° C. are satisfactory but temperatures as low as 25° C. and as high as 200° C. have been used with good results.

The monodecarboxylation can be applied to the solid diacid or in solution in a polar solvent, such as dimethyl sulfoxide. Pressure can be used to maintain the solvent liquid if the temperature is to exceed its boiling point.

The ester hydrolysis and decarboxylation steps represent a considerable improvement over the prior procedure using NaCN in dimethylsulfoxide to cleave the ester groups of VII-3 and effect decarboxylation, proceeding directly to form VII-4. This requires considerably higher temperatures, exceeding 180°–200° C., giving poor yields of dark-colored products.

The second stage of the synthesis proceeds using known steps from the monocarboxylic acid VII-5 to the corresponding 10-deazaaminopterin or 5,10- or 8,10-dideazaaminopterin, and is shown in Reaction Schemes 2 and 4–6.

Pharmaceutical Compositions

Compounds of the current invention are useful in the method of treatment of rheumatoid arthritis and as active neoplastic agents.

The 5-deazaaminopterins and 5,10-dideazaaminopterins compounds of the current invention can be administered per se, or in association with a pharmaceutically acceptable diluent or carrier. The invention accordingly also provides a pharmaceutical composition in dosage unit form comprising from 0.1 to about 500 mg of deazaaminopterin compound of the invention, per dosage unit, together with a pharmaceutically acceptable nontoxic inert excipient, carrier or diluent.

The 5-deazaaminopterin and 5,10-dideazaaminopterin compounds can be formulated in the form of an acid addition salt. These salts are formed with one or more free $NH_2$ groups of the heteroaroyl-10-deazaaminopterin molecule. Typically, the compounds are injected in the form of their sodium salts in aqueous solution. Other salts, such as K, Ca, $NH_4$, and the like, could be used as prepared from the appropriate hydroxide or carbonates.

The acid addition salts are the pharmaceutically acceptable, nontoxic addition salts with suitable acids, such as those with inorganic acids, for example, hydrochloric, hydrobromic, nitric, sulfuric, and phosphoric acids, and with organic acids, such as organic carboxylic acids, for example, glycolic, maleic, hydroxymaleic, malic, tartaric, citric, salicylic, acetyloxybenzoic, nicotinic, and isonicotinic acid, and organic sulphonic acids, for example, methanesulphonic, ethanesulphonic, 2-hydroxyethanesulphonic, toluene-p-sulphonic, and naphthalene-2-sulphonic acid.

An acid addition salt can be converted into the free compound according to known methods, for example, by treating it with a base, such as with a metal hydroxide or alkoxide, for example, an alkali metal or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example, sodium, potassium or calcium carbonate or hydrogen carbonate, with ammonia or with a hydroxyl ion exchange resin, or with any other suitable reagent.

An acid addition salt may also be converted into another acid addition salt according to known methods. For example, a salt with an inorganic acid may be treated with a metal salt, such as for example a sodium, barium or silver salt, of an acid in a suitable diluent, in which a resulting inorganic salt is insoluble and is thus removed from the reaction medium. An acid-addition salt may also be converted into another acid addition salt by treatment with an anion exchange preparation.

The glutamic acid COOH groups can also be in salt form, as the ammonium $NH_4$, alkali metal salts ($Na^+$, $K^+$), or the nontoxic alkaline earth metal salts ($Ca^{++}$) of the glutamate COOH groups.

The 5-deazaaminopterin or 5,10-dideazaaminopterin compound or salt thereof can be administered to the mammal, including human, by any available route, including oral and parenteral (intravenous, intraperitoneal, subcutaneous, and intramuscular) administration. The amount administered is sufficient to ameliorate the arthritis or other proliferative disease, leukemia or other tumors. The amount will depend upon the type of disease, and on the weight of the patient. For example, in human administration, a dosage of 5-deazaaminopterin or 5,10-deazaaminopterin compound is within the range from about 0.1 mg/kg to about 500 mg/kg per day. Dosages exceeding the higher part of the range are administered in conjunction with leucovorin, 5-formyl tetrahydrofolate, to reduce toxicity. The upper limit of dosage is imposed by toxic side effects.

To facilitate administration, the deazaaminopterin compound or salt thereof can be provided in composition form, and preferably in dosage unit form. While the compound can be administered per se, it is normally administered in conjunction with a pharmaceutically acceptable carrier therefor, which dilutes the compound and facilitates handling. The term "pharmaceutically acceptable" means that the carrier (as well as the resulting composition) is sterile and nontoxic.

The carrier or diluent can be solid, semisolid, or liquid, and can serve as a vehicle, excipient, or medium for the 5-deazaaminopterin or 5,10-dideazaaminopterin compound. Exemplary diluents and carriers include lactose, dextrose, sucrose, sorbitol, mannitol, starches, gun acacia, calcium phosphate, mineral oil, cocoa butter, oil of theobroma, alginates, tragacanth, propylhydroxy-benzoate, talc, or magnesium stearate.

For convenience in handling, the 5-deazaaminopterin or 5,10-dideazaaminopterin compound and carrier or diluent can be enclosed or encapsulated in a capsule, sachet, cachet, gelatin, paper or other container, especially when intended for use in dosage units. The dosage units can for example take the form of tablets, injections, capsules, suppositories, or cachets.

UTILITY

Compounds of the current invention are useful for treatment and prevention of arthritis, particularly rheumatoid arthritis, for suppression of neoplastic growth in tumors, such as mammary tumors, and for suppression of neoplastic growth of blood forming tissues, particularly for treatment of leukemia.

The biological activity of the compounds of the current invention was tested in vitro in culture cells and in vivo in mammals.

The antiarthritic efficacy evaluation used a mouse model of inflammatory disease that occurs in response to an antigenic challenge with Type II collagen according to method described in *Nature*, 283, 666–668 (1980).

The fundamental aspects of the mouse model allow it to serve as a representative presentation of human disease. The parallels between the known aspects of the mouse model and rheumatoid arthritis include a humoral response in which antibodies are produced to an antigen that is present in the joint tissue and the antigenic challenge is accompanied by cell-mediated aspects of immunity. The resultant inflammation of the joint tissue yields facets of periostitis, synovial lining hyperplasia, degradation of bone and cartilage and pannus and new bone formation.

Antineoplastic activity of the compounds of the current invention was tested by the effect of these compounds on growth inhibition of L 1210 murine leukemia cells in culture.

The following Examples are intended to illustrate the preparation of representative compounds, methods and procedures of this invention. They are not to be interpreted to limit the scope of this invention in any way.

EXAMPLE 1

Preparation of 5-Propyl-5-deazaaminopterin (21a)

This example illustrates preparation of N-[4-([2,4-diamino-5-propylpyrido[2,3-d]pyrimidine-6-yl)methyl]amino) benzoyl]-L-glutamic Acid (5-propyl-5-deazaaminopterin), according to the procedure illustrated in the Reaction Scheme 1. The compound is listed in the Table 1 as compound 21a.

2-Amino-6-chloro-4-propyl-3,5-pyridinedicarbonitrile(I,2a)

A solution of trimethylorthobutyrate I-1a (100 g, 0.670 mol), malononitrile (89.1 g, 1.35 mol), and pyridine (270 mL) was refluxed for 1 hour. Excess pyridine was then removed by evaporation under reduced pressure ($H_2O$ aspirator, bath to 60° C.). The residue was treated with 12N HCl (1.15 L) and the mixture was transferred to a 5-L three-necked flask equipped with a thermometer, condenser, and mechanical stirrer (Teflon paddle). The mixture was stirred rapidly while being heated at 85°–90° C. for 1 hour. Solid material formed during this time. The mixture was cooled to 20°–25° C., and cold $H_2O$ (3 L) was added. After the mixture had been kept in a refrigerator overnight, the solid was collected, washed thoroughly with $H_2O$ and dried in vacuo. The product I-2a was homogeneous according to thin-layer chromatography (TLC) (EtOAc-cyclohexane, 1:1); yield 28% (42.4 g).

Spectral data: mass, m/z 221, $MH^+$ for $C_{10}H_9ClN_4$.

2-Amino-4-propyl-3,5-pyridinedicarbonitrile I-3a)

A solution of I-2a (42.3 g, 0.193 mol) in dimethylformamide (DMF) (600 mL) and triethylamine ($Et_3N$) (70 mL) containing $PdCl_2$ (1.1 g) was shaken on a Parr apparatus under $H_2$ at 45 psi for 16 hours. Examination by TLC revealed that conversion was incomplete. The mixture was filtered from catalyst with the aid of a little DMF. Fresh $PdCl_2$ (1.1 g) and more $Et_3N$ (35 mL) were added to the filtrate, and hydrogenation at 45 psi was resumed. After 3 hours, TLC showed that the compound I-2a had been completely converted. The mixture was filtered and the filtrate was concentrated under reduced pressure (<1 mm, bath 30° C.) to about 75–100 mL. Dilution with cold $H_2O$ (1 L) caused precipitation of product I-3a; yield 91% (32.6 g), homogeneous by TLC.

Spectral data: mass, m/z 187, $MH^+$ for $C_{10}H_{10}N_4$; $^1H$ NMR ($Me_2SO-d_6$) d 0.95 (t, 3, $CH_3$), 1.65 (m, 2, $CH_2$), 2.75 (t, 2, $CH_2$), 7.88 (br s, 2, $NH_2$), 8.52 (s, 1, $C^6$—H).

2,4-Diamino-5-propylpyrido[2,3-d]pyrimidine-6-carbonitrile (I-4a)

Anhydrous guanidine•HCl (6.15 g, 0.064 mol) and NaOMe (3.49 g, 0.065 mol) were combined in dry 2-(2-methoxyethoxy) ethanol (270 mL), and the mixture was stirred for about 0.5 hour before it was combined with a solution of compound I-3a (12.0 g, 0.064 mol) in 2-(2-methoxyethoxy)ethanol (335 mL). The stirred mixture was heated under $N_2$ at 150°–160° C. for 7 hours. This mixture was allowed to cool to about 110° C. while another solution of guanidine (one-half the previous amount) in 2-(2-methoxyethoxy)ethanol was prepared. The second guanidine solution was added, and heating at 150°–160° C. was resumed. After 5 hours, the mixture was allowed to cool, then evaporated in vacuo (<1 mm) to a viscous mixture. Addition of cold $H_2O$ (~500 mL) gave a crude solid, which was collected and dried in vacuo. The crude product mixture (11.4 g) was dissolved in DMF, and the solution was swirled with silica gel (about 40 g of 60–200 mesh). Evaporation in vacuo as before gave a solid dispersion of crude product mixture and silica gel. The dispersion was pulverized, dried further in vacuo, then applied to a column (9×50-cm) of silica gel (60–200 mesh poured from $CHCl_3$) and gravity elution by $CHCl_3$—MeOH (95:5) was performed. Homogeneous fractions ($R_f$~0.55 on TLC using $CHCl_3$—MeOH, 5:1) were combined and evaporated to give pure product I-4a (3.3 g, 23% yield).

Spectral data: mass, m/z 229, $MH^+$ for $C_{11}H_{12}N_6$; $^1H$ NMR ($Me_2SO-d_6$) δ 0.92 (t, 3, $CH_3$), 1.62 (m, 2, $CH_2$ $\underline{CH_2}CH_3$), 3.20 (m, 2, $\underline{CH_2}CH_2CH_3$), 6.8–7.0 (br, 2, $NH_2$), 7.32 (br s, 2, $NH_2$), 8.78 (s, 1, $C^7$—H).

Diethyl N-[4-([(2,4-Diamino-5-propylpyrido[2,3-d]pyrimidine-6-yl)methyl]amino)-benzoyl]-L-glutamate (I-5a)

A stirred solution of I-4a (1.21 g, 5.30 mmol) and diethyl N-(4-aminobenzoyl)-L-glutamate (2.33 g, 7.23 mmol) in glacial AcOH (250 ml) containing damp Raney Ni (about 8 g) was kept under $H_2$ at atmospheric pressure for approximately 4 hours until $H_2$ absorption had ceased. The catalyst was removed by filtration, and the filtrate was evaporated ($H_2O$ aspirator, bath 30° C.). The residue was dissolved in the minimum volume of EtOH (12–15 mL), and the stirred solution was gradually treated with 3% $Na_2CO_3$ solution to pH 7.8. The resulting crude product mixture was collected with the aid of cold $H_2O$, dried, and dispersed onto silica gel (60–200 mesh) as described above for precursor I-4a. The dispersion was applied to a silica gel column (5×50-cm) poured from $CHCl_3$ and eluted by gravity flow with $CHCl_3$—MeOH (95:5). After TLC showed that all diethyl N-(4-aminobenzoyl)-L-glutamate and minor contaminants more mobile than product I-5a had been eluted, the system was switched to 85:15 CHCl$_3$—MeOH. Homogeneous fractions (R$_f$-0.5 using CHCl$_3$—MeOH, 3:1) were combined and evaporated to give pure product I-5a in 16% yield (470 mg).

Spectral data: Mass, m/z 538, MH$^+$; $^1$H NMR δ 0.92 (t, 3, CH$_3$), 1.12–1.22 (2 t, 6, CH$_3$CH$_2$O overlapping), 1.54 (m, 2, CH$_2$CH$_2$CH$_3$), 1.98 and 2.06 (m, 2, glu-3-CH$_2$), 2.42 (t, 2, CH$_2$CH$_2$CO), 3.02 (t, 2, CH$_2$CH$_2$CH$_3$), 4.00–4.14 (br m, 4, CH$_3$CH$_2$O), 4.32 (d, 2, CH$_2$NH), 4.38 (m, 1, CONHCH ), 6.35 (br s, 2, NH$_2$), 6.56 (t, 1, 10-NH), 6.66 and 7.68 (2 d, 4, C$_6$H$_4$), 7.05 (s, 2, NH$_2$), 8.25 (d, 1, CONH), 8.52 (s, 1, C$^7$—H). Anal. Calcd. for C$_{27}$H$_{35}$N$_7$O$_5$° 0.5 H$_2$O; C, 59.33; H, 6.64; N, 17.94. Found: C, 59.24, H, 6.56, N, 17.68.

N-[4-[[(2,4-Diamino-5-propylpyrido[2,3-d]pyrimidine-6-yl)methyl]amino]benzoyl]-L-glutamic Acid (21a)

A solution of I-5a (400 mg, 0.732 mmol) in MeOH (800 mL) was treated with 1N NaOH (1.7 ml). The solution was kept at 20°–25° C. for 4 days. MeOH was removed by evaporation under reduced pressure (H$_2$O aspirator, bath 20°–25° C.). The aqueous residue (adjusted to 50 ml) was treated again with 1N NaOH (0.8 ml). After reaction proceeded for 4–5 more days at 20°–25° C. HPLC showed that conversion of I- 5a to product compound 21a was complete. The solution was clarified (Norit, Celite) and treated with 1N HCl to precipitate compound 21a at pH 3.8 as a pale beige solid; yield, 69% (260 mg). Assay by HPLC showed the product to be homogeneous.

Spectral data: Mass, m/z 482, MH$^+$; UV, 228 nm (ε 38,300), 299 (22,500) at pH 1; 225 nm (ε 34,400), 284 (26,500) at pH 7; 225 nm (ε 32,000), 284 (26,700) at pH 13; $^1$H NMR (Me$_2$SO—d$_6$) δ 0.92 (t, 3, CH$_3$), 1.56 (m, 2, CH$_2$CH$_2$CH$_3$), 1.96 and 2.02 (m, 2, glu-3-CH$_2$), 2.32 (t, 2 CH$_2$CH$_2$CO), 3.4 (t, 2, CH$_2$CH$_2$CH$_3$), 4.30 (d, 2 CH$_2$NH), 4.32 (m, 1, CONHCH), 6.54 (t, 1, CH$_2$NH), 6.64 and 7.66 (2 d, 4, C$_6$H$_4$), 6.65 (br, 2 NH$_2$), 7.24 (br, 2 NH$_2$), 8.06 (d, 1, CONH), 8.52 (s, 1, C$^7$—H) . Anal. Calcd. for C$_{23}$H$_{27}$N$_7$O$_5$° 2 H$_2$O: C, 53.38; H, 6.04; N, 18.94. Found: C, 53.61; H, 5.84; N, 18.75.

EXAMPLE 2

Synthesis of 5-Butyl-5-Deazaaminopterin (25a)

This example illustrates a preparation of N-[4-[(2,4 -diamino-5-butylpyrido [2,3-d]pyrimidine-6-yl)-methyl] amino]benzoyl-L-glutamic acid (5-butyl-5 -deazaaminopterin), according to the procedure illustrated in the Reaction Scheme 1. Example yields compound 25a listed in Table 1.

2-Amino-6-chloro-4-butyl-3,5-pyridinedicarbonitrile (I-1b)

A solution of trimethyl orthovalerate I-1b (20.1 g, 0.124 mol) and malononitrile (16.4 g, 0.248 mol) in pyridine (50 mL) was refluxed 45 min, cooled, and evaporated. The residue was stirred with 12N HCl (210 mL) at 85° C. (bath temp) for 45 min to give product I-2b as an insoluble solid. After dilution with H$_2$O (100 mL), the mixture was chilled and the solid collected to give product I-2b in 27% yield (7.96 g); homogeneous by TLC (cyclohexane-EtOAc, 1:1).

Spectral data: Mass, m/z 235, MH$^+$ for C$_{11}$H$_{11}$ClN$_4$.

2-Amino-4-butyl-3,5-pyridinedicarbonitrile (I-3b)

Hydrogenolysis of I-2b (7.32 g, 31.2 mmol) in DMF (88 ml) containing PdCl$_2$ and Eton (9 ml) was conducted in a Parr shaker at 40 psi for 16 hours. Examination by TLC revealed absence of precursor of I-2b. The catalyst was removed by filtration, and the filtrate was diluted with H$_2$O to cause precipitation of compound I-3b. The collected solid was reprecipitated from a Norit-treated and filtered (Celite) solution in DMF (120 ml) by adding H$_2$O. A yield of product I-3b was 90% (5.6 g); homogeneous by TLC (cyclohexane-ETOAc, 1:1).

Spectral data: Mass, m/z 201, MH$^+$ for C$_{11}$H$_{12}$N$_4$; $^1$H NMR (Me$_2$SO—d$_6$) δ 0.92 (t, 3, CH$_3$), 1.38 (m, 2, CH$_2$CH$_2$CH$_2$CH$_3$), 1.58 (m, 2, CH$_2$CH$_2$CH$_2$CH$_3$), 2.75 (t, 2, CH$_2$CH$_2$CH$_2$CH$_3$), 7.88 (br, 2, NH$_2$), 8.52 (s, 1, C$^6$—H).

2,4-Diamino-5-butylpyrido[2,3-d]pyrimidine-6-carbonitrile (I-4b)

The annulation of compound I-3b with guanidine was conducted as described for the conversion of compound I-3a to I-4a in Example 1. A typical yield of pure product I-4b after column chromatographic purification as described in Example 1 was 20%; homogeneous by TLC (CHCl$_3$—MeOH, 7:1).

Spectral data: Mass, m/z 342, MH$^+$ for C$_{12}$H$_{14}$N$_6$; $^1$H NMR δ 0.88 (t, 3, CH$_3$), 1.34 (m, 2, CH$_2$CH$_2$CH$_2$CH$_3$), 1.56 (m, 2, CH$_2$CH$_2$CH$_2$CH$_3$), 3.24 (t, 2, CH$_2$CH$_2$CH$_2$CH$_3$), 6.9 (br, 2, NH$_2$), 7.34 (br, 2, NH$_2$), 8.76 (s, 1,) C$^7$—H.

Diethyl N-[4-[[(2,4-Diamino-5-butylpyrido[2,3-d] pyrimidine-6-yl)methyl] amino]-benzoyl-L-glutamate (I-5b)

Reductive condensation of precursor I-4b with diethyl N-(4-aminobenzoyl)-L-glutamate was conducted as described in Example 1 for I-4a. Pure product I-5b was isolated as described in Example 1. A yield of pure 5b was 15%.

Spectral data: Mass m/z 552, MH$^+$ for C$_{28}$H$_{37}$N$_7$O$_5$; $^1$H NMR (Me$_2$SO—d$_6$) δ 0.85 (t, 3, CH$_3$), 1.12–1.22 (2 t, 6, CH$_3$CH$_2$O), 1.35 (m, 2, CH$_2$CH$_2$CH$_2$CH$_3$), 1.52 (m, 2, CH$_2$CH$_2$CH$_3$), 1.98 and 2.05 (2 m, 2, glu-3-CH$_2$), 2.42 (t, 2, CH$_2$CH$_2$CO), 3.04 (t, 2, CH$_2$CH$_2$CH$_2$CH$_3$), 4.0–4.15 (br m, 4, CH$_3$CH$_2$O), 4.30 (d, 2, CH$_2$NH), 4.38 (m, 1, CONHCH), 6.24 (br s, 2, NH$_2$), 6.52 (t, 1, 10—NH), 6.66 and 7.68 (2 d, 4, C$_6$H$_4$), 6.92 (br s, 2, NH$_2$), 8.24 (d, 1, CONH), 8.40 (s, 1, C$^7$—H).

N-[4-[(2,4,Diamino-5-butylpyrido[2,3-d]pyrimidine-6-yl)methyl]amino]benzoyl-L-glutamic Acid (25a )

A solution of precursor I-5b (50 mg, 0.091 mmol) in MeOH (150 ml), treated with 1N NaOH (0.24 ml) was kept at 20°–25° C. for 4 days. MeOH was evaporated in vacuo (H$_2$O aspirator, bath 25° C.), and the residue was dissolved in H$_2$O (3 mL). After 30 hours at 20°–25° C., the solution was carefully treated with 1N HCl to pH 3.8, where the product 25a precipitated; yield, 51% (24 mg). Assay by HPLC showed the product to be of 99.4% purity.

Spectral data: Mass, m/z 496, MH$^+$; UV, 300 nm (ε 23,900) at pH 1; 287 nm (ε 25,900) at pH 7; 287 nm (ε 26,100) at pH 13; $^1$H NMR (Me$_2$SO—d$_6$) δ 0.85 (t, 3, CH$_3$), 1.35 (m, 2, CH$_2$CH$_2$CH$_2$CH$_3$), 1.52 (m, 2, CH$_2$CH$_2$CH$_2$CH$_3$), 1.96 and 2.02 (2 m, 2, glu-3-CH$_2$), 2.32 (t, 2, CH$_2$CH$_2$CO), 3.06 (t, 2, CH$_2$CH$_2$CH$_2$CH$_3$), 4.3 (m, 3, CH$_2$NH overlapping with CONHCH), 6.54 (t, 1, 10—NH), 6.66 and 7.66 (2 d, 4, C$_6$H$_4$), 7.18 (br s, 2, NH$_2$), 8.08 (d, 1, CONH), 8.54 (s, 1 C$^7$H). Anal. Calcd. for C$_{24}$H$_{29}$N$_7$O$_5$° 1.5 H$_2$O: C, 55.17; H, 6.17; N, 18.76. Found: C, 55.12; H, 6.03; N, 18.59.

EXAMPLE 3

Synthesis of N-[5-([2,4-Diaminopyrido[2,3-d]pyridin-6-yl) methyl]amino)thiophene-2-carbonyl]-L-glutamic Acid (29)

This example illustrates preparation of N-[5-([[(2,4-diaminopyrido[2,3-d]pyridin-6-yl)methyl]amino)thiophene-2-carbonyl]-L-glutamic Acid (29) prepared according to the procedure illustrated in Reaction Scheme 3.

6-(Bromomethyl)-2,4-diaminopyrido[2,3-d] pyrimidine (III-2, where R$_1$ is hydrogen)

The intermediate III-2 was prepared from 2,4-diaminopyrido [2,3-d]pyrimidine-6-methanol (III-1) by the procedure described in *J. Med. Chem.*, 35:332 (1992). This particular preparation analyzed for a 1.75 HBr° 0.25 CH$_3$COOH salt (formula wt. 406.7). The material was suitable for conversions to compound 33.

N-(5-Aminothiophene-2-carbonyl)-L-glutamic Acid Diethyl Ester (III-3), R$_2$=H This compound was prepared by the method described in *J. Med. Chem.*, 34:1594 (1991).

N-[5-[(2,4-Diaminopyrido[2,3-d]pyridin-6 -yl)methyl]amino)thiophene-2-carbonyl]-L-glutamic Acid (29).

6-(bromomethyl)-2,4-diaminopyrido [2,3-d] pyrimidine (III-2) R$_2$=H, and the sidechain precursor N-(5-aminothiophene-2-carbonyl)-L-glutamic acid diethyl ester (III-3) R$_2$=H (1.2 mmol of each) were stirred with CACO$_3$ (2.4 mmol) in Me2NAc (15 mL) at 20°–25° C. for 4 days. The mixture was filtered, and the clear filtrate was added dropwise to excess 2.5% NaHCO$_3$ solution with stirring. The formed precipitate was collected, dried, and chromatographed on silica gel with elution by CHCl$_3$—MeOH (2:1) to give essentially pure diethyl ester (III-4a), 91 mg (15%).

Mass spectrum, m/e 502 (MH+ for C$_{22}$H$_{27}$N$_7$O$_5$S); >92% by HPLC.

For hydrolysis, the ester (90 mg) was stirred with 1 N NaOH (1.8 mL) for 5 h (solution occurred after 1.5 h). Acidification to pH 3.8 caused precipitation of the product; N-[5-([[(2,4-diaminopyrido[2,3-3] pyridine-6-yl) methyl] amino)thiophene-2-carbonyl]-L-glutamic acid III- 5a, compound 29. Yield 67 mg (75%), Mass spectrum, m/e 446, MH+ for C$_{18}$H$_{19}$N$_7$O$_5$S.

EXAMPLE 4

Synthesis of N-[5-[(2,4-Diamino-5-methylpyrido [2,3,d]pyrimidine-6-yl)methyl]amino] thiophene-2-carbonyl]-L-glutamic Acid This example illustrates preparation of N-[5-([(2,4-diamino-5-methylpyrido[2,3-d]pyrimidine-6-yl)methyl] amino) thiophene-2-carbonyl]-L-glutamic Acid (39) as seen in Table 1, wherein R$_1$ is methyl, by the procedure illustrated in Reaction Scheme 3.

6-(Bromomethyl)-2,4-diamino-5-methylpyrido-[2,3-d]pyrimidine (III-2, wherein R$_1$ is C$_3$)

2,4-Diamino-5-methylpyrido[2,3-d]pyrimidine-6-methanol, (III-1), prepared according *J. Med. Chem.*, 35:3002 (1992) (4.5 g, 22.0 mmol) was dissolved in glacial AcOH (200 mL) at 95° C. The solution was cooled to 25° C. then treated with stirring with 30% dry HBr in AcOH (400 mL). When addition was complete, a clear solution remained. The flask was stoppered securely, and the solution was kept at 20°–25° C. before it was added to ethanol (2.2 L) with stirring. The precipitate that formed was collected under N$_2$, washed with ethanol, and dried in vacuo (P$_2$O$_5$ and NaOH pellets); yield 9.5 g of product 6-bromomethyl-2,4-diamino-5-methylpyrido[2,3-d] pyrimidine (III-2), R$_1$=CH$_3$ hydrobromide solvated by AcOH; yield 99% (based on formulation shown below).

Mass spectrum, m/e 268 and 270, MH+ for C$_9$H$_{10}$BrN$_5$; 1H NMR (Me$_2$SO—d$_6$) δ 2.78 (s, 3, CH$_3$), 4.93 (s, 2, CH$_2$Br), 8.17 (s, 2, NH$_2$), 8.75 (s, 1, C$_7$H), 9.32 (s, 2, NH$_2$); solvation by 0.5 CH$_3$CO$_2$H evidenced by methyl-group singlet at 1.90.

Anal. Calcd for C$_9$H$_{10}$BrN$_5$ 1.7HBr 0.5CH$_3$CO$_2$H (formula wt. 435.7): C, 27.57; H, 3.17; N, 16.07. Found: C, 27.53, H, 3.37; N, 16.11.

N-[5-([(2,4-Diamino-5-methylpyrido[2,3-d]pyrimidine-6 -yl)methyl]amino)thiophene-2-carbonyl]-L-glutamic Acid (43)

Bromomethyl compound (III-2, wherein R$_1$=CH$_3$) (3.5 g, 8.0 mmol), sidechain precursor N-(5-aminothiophene-2-carbonyl)-L-glutamic acid diethyl ester (III-3, wherein R$_2$ is H) (2.7 g, 8.2 mmol), and CaCO$_3$ (1.63 g, 16.3 mmol) were combined in Me$_2$NAc (50 mL). The stirred mixture was warmed briefly (5–10 min) at 70° C. Reactants other than CaCO$_3$ dissolved readily. The mixture was stirred at 20°–25° C. in a stoppered flask under N$_2$ for 7 days. Inorganic matter was filtered off, and silica gel (25 g) was added to the filtrate. The slurry was evaporated in vacuo, and the dispersion was pulverized for application on a silica gel column (4×50 cm). Elution by CHCl$_3$—MeOH (95:5) removed front-running impurities. The product was eluted with CHCl$_3$—MeOH (85:15). Appropriate fractions were combined and evaporated to give the diethyl ester III-4b (3.4 g, 81% yield). Mass spectrum, m/e 516, MH+ for C$_{23}$H$_{29}$N$_7$O$_5$S.

The diethyl ester III-4b (258 mg, 0.50 mmol) was stirred for 3 hours under N$_2$ with 1N NaOH (5.0 mL). The resulting clear solution was treated with 2N HCl to pH 3.5 to give pure compound 39 (III-5b); yield 46% (0.11 g).

Mass spectrum, 460, MH+; 1H NMR (Me$_2$SO—d6) δ 1.88, 1.98 (m, 2, glu-3-CH$_2$), 2.30 (t, 2, CH$_2$CO), 2.66 (s, 3, CH$_3$), 4.25 (m, 1, CHNH), 5.94 (d, 1, 4-ArH) 6.68 (s, 2, NH$_2$), 7.2–7.35 (m, 3, NH$_2$ overlapping 5-ArNH), 7.48 (d, 1, 3-ArH), 7.98 (d, 1, CONH), 8.52 (s, 1, C7-H).

Anal. Calcd for C$_{19}$H$_{21}$N$_7$O$_5$S° 2.8H$_2$O: C, 44.74; H, 5.26; N, 19.23. Found: C, 44.78; H, 5.18; N, 19.49.

EXAMPLE 5

Synthesis of N-[5-([[(2,4-Diamino-5-methylpyrido [2,3-d]pyrimidine-6-yl) methyl]methylamino)thiophene- 2-carbonyl]-L-glutamic Acid (40)

This example illustrates a preparation of N-[5-[[(2,4-Diamino-5-methylpyrido[2,3-d]pyrimidine-6-yl) methyl]methylamino)thiophene-2-carbonyl]-L-glutamic acid (40) wherein both $R_1$ and $R_2$ are methyl, according to the procedure illustrated in the Reaction Scheme 3.

N-[5-(Methylamino)thiophene-2-carbonyl]-L-glutamic Acid Diethyl Ester (III-3, where $R_2$ is $CH_3$)

A solution containing N-(5-aminothiophene-2-carbonyl)-L-glutamic acid diethyl ester (III-3 where $R_2$ is H) (1.78 g, 5.42 mmol), (i-Pr)$_2$NEt (1.0 mL, 0.74 g, 5.7 mmol), and Me$_2$SO$_4$ (0.59 mL, 0.79 g, 6.2 mmol) in 20 mL N,N-dimethylformamide (DMF) was warmed at 60° C. for 2 hours, then left at 20°–25° C. for 42 hours. The solution was evaporated in vacuo (1 mm, bath 25°–30° C.), and the residue was dissolved in EtOAc-cyclohexane (1:1 by volume) for application to a silica gel column. Elution by the same solvent system afforded fractions homogeneous by TLC of the product. Fractions were combined and evaporated to afford 16% yield (287 mg) of N-[5-(methylamino)thiophene-2-carbonyl]-L-glutamic acid diethyl ester (III-3) $R_2$=$CH_3$ as an amber oil.

Mass spectrum, m/e 343, MH+ for $C_{15}H_{22}N_2O_5S$.

N-[5-([(2,4-Diamino-5-methylpyrido[2,3-d]pyrimidine-6-yl)methyl]methylamino)thiophene-2-carbonyl-L-glutamic Acid (40)

The compound 40 was prepared from 6-(bromomethyl)-2,4-diaminopyrido [2,3-d]pyrimidine III-2 where $R_1$ is $CH_3$ (0.91 mmol) and from sidechain precursor N-[5-(methylamino) thiophene-2-carbonyl]-L-glutamic acid diethyl ester III-3, where $R_2$ is $CH_3$ (0.96 mmol) by essentially the same procedure as described above for the preparation of compound 39. After filtration, the reaction solution was evaporated (<1 mm, bath to 40° C.). The residue was dissolved in CHCl$_3$—MeOH (6:1) for application to a silica gel column. Elution by CHCl$_3$—MeOH (6:1) gave fractions homogeneous by TLC (CHCl$_3$—MeOH, 4:1; $R_f$~0.5) which were combined and evaporated to give the diethyl ester of N-[5-([(2,4-diamino-5-methylpyrido [2,3-d]pyrimidine-6-yl) methyl]methylamino]thiophene-2-carbonyl]-L-glutamic acid (III-4c); yield 27% (132 mg).

Mass spectrum, m/e 530, MH+ for $C_{24}H_{31}N_7O_5S$.

The compound III-4c was hydrolyzed as previously described to give pure compound N-[5-([(2,4-diamino-5-methylpyrido [2,3-d]pyrimidine-6-yl) methyl]methylamino) thiophene-2-carbonyl]-L-glutamic acid (40) in 80%; yield (109 mg).

Mass spectrum, m/e 474, MH+; 1H NMR (Me$_2$SO—d6) δ 1.90, 2.00. (m, 2, glu-3-CH$_2$), 2.32 (t, 2, CH$_2$CO), 2.60 (s, 3, 5 -CH$_3$), 2.87 (s, 3, CH$_3$N), 4.30 (m, 1, CHNH), 4.50 (s, 2, CH$_2$N), 6.05 (d, 1, 4-ArH), 6.68 (s, 2, NH$_2$), 7.32 (s, 2, NH$_2$), 7.58 (d, 1, 3-ArH), 8.06 (d, 1, CONH), 8.35 (s, 1, C7H). Anal. Calcd for $C_{20}H_{23}N_7O_5S$° 3H$_2$O: C, 45.53; H, 5.54; N, 18.59. Found: C, 45.60; H, 5.28; N, 18.36.

EXAMPLE 6

Preparation of N-[5-([(2,4-Diamino-5-Ethylpyrido[2,3-d]-Pyrimidine-6-yl) Methyl]Methylamino) Thiophene-2-Carbonyl]L-Glutamic Acid (47)

This example illustrates a preparation of N-[5-([2,4 -diamino-5-ethylpyrido[2,3-d]-pyrimidine-6-yl) methyl]methylamino]thiophene-2-carbonyl]-L-glutamic acid according to the procedure illustrated in the Reaction Scheme 3, resulting in compound 47 seen in Table 2.

6-(Bromomethyl)-2,4-diamino-5-ethylpyrido[2,3-d]pyrimidine (III-2, where $R_1$ is ethyl)

2,4-Diamino-5-ethylpyrido[2,3-d]pyrimidine-6-methanol (2.80 g, 12.8 mmol), prepared as described in Examples 1 and 2 for the 5-CH$_3$ homolog, was converted to 6 -(bromomethyl)-2,4-diamino-5-ethylpyrido[2,3-d]pyrimidine compound (III-2, where $R_1$ is ethyl) as described above for 6-(bromomethyl)-2,4-diaminopyrido [2,3-d]pyrimidine compound (III-2, where $R_1$ is H) yielding 5.3 g.

Mass spectrum, m/e 282 and 284, MH+ for $C_{10}H_{12}BrN_5$; 1H NMR (MeSO—d6) δ 1.24 (t, 3, CH$_3$), 3.24 (q, 2, CH$_2$), 4.94 (s, 2, CH$_2$Br), 8.14 (s, 2, NH$_2$), 8.80 (s, 1, C7—H), 9.22 (s, 2, NH$_2$); solvation by ⅓ CH$_3$CO$_2$H was evidenced by a methyl-group singlet at 1.92.

N-[5-[[(2,4-Diamino-5-ethylpyrido[2,3-d]-pyrimidine-6-yl) methyl]methylamino]thiophene-2-carbonyl]-L-glutamic acid (47)

Alkylation of N-[5-(methylamino)thiophene-2-carbonyl] -L-glutamic acid diethyl ester product (III-3, where $R_2$ is $CH_3$) by 6-(bromomethyl)-2,4-diamino-5-ethylpyrido [2,3-d]pyrimidine compound III-2, where $R_1$ is ethyl (0.84 mmol of each) was done as described for the preparation of compound 39. Purification of the ester produced (III-4d) was done as described in Example 5 with CHCl$_3$—MeOH (7:1) used as eluant. The yield of pure diethyl ester of N-[5-[[(2,4 -diamino-5-ethylpyrido [2,3-d]-pyrimidine-6-yl) methyl] methylamino]thiophene-2-carbonyl]-L-glutamic acid (III-4d) was 27% (124 mg).

Mass spectrum, m/e 544, MH+ for $C_{25}H_{33}N7O_5S$.

The compound III-4d was hydrolyzed as described for compound 43 in Example 4, to give compound N-[5-([(2,4 -diamino-5-ethylpyrido [2,3-d]-pyrimidine-6-yl) methyl] methylamino)thiophene-2-carbonyl]-L-glutamic acid (47) in 82% yield (102 mg).

Mass spectrum, m/e MH+; 1H NMR (Me$_2$SO—d6) δ 1.16 (t, $\underline{CH_2}$CH$_2$), 1.90, 2.00 (m, 2, glu-3-CH$_2$), 2.30 (t, 2, CH$_2$CO), 2.86 (s, 3, CH$_3$N ), 3.00 (q, 2, CH$_3$CH$_2$), 4.28 (m, CHNH), 4.52 (s, 2, CH$_2$N), 6.05 (d, 1, 4-ArH), 6.60 (s, 2, NH$_2$), 7.22 (s, 2, NH$_2$), 7.61 (d, 1, 3-ArH), 8.06 (d, 1, CONH), 8.40 (s, 1, C7H). Anal. Calcd for $C_{21}H_{25}$,$_7$N$_7$O$_5$S 3H$_2$O: C, 46.57; H, 5.77; N, 18.10. Found: C, 46.55,; H, 5.52; N, 18.15.

EXAMPLE 7

Preparation of N-[5-([(2,4-Diamino-5-Propylpyrido-[2,3-d] Pyrimidine-6-yl)Methyl]Amino])Thiophene-2-Carbonyl]L-Glutamic Acid (49)

This example illustrates a preparation of N-[5-([(2,4 -diamino-5-propylpyrido[2,3-d]pyrimidine-6-yl) methyl]amino)thiophene-2-carbonyl]L-glutamic acid according to the procedure illustrated in the Reaction Scheme 3, resulting in compound 49 in Table 2.

2,4-Diamino-5-propylpyrido[2,3-d]pyrimidine-6-carboxaldehyde

Raney Ni (1.2 g damp) was added with the aid of 95–97% HCO$_2$H (7 mL) to a solution of 2,4-diamino-5-propylpyrido [2,3 -d]pyrimidine-6-carbonitrile (I-4a) (500 mg, 2.19 mmol) in 95–97% HCO$_2$H (5 mL). The stirred mixture was heated at 75°–80° C. for 1.5 h. Raney Ni was removed by filtration, and the filtrate was evaporated. The residue was dissolved in hot $H_2O$ (20 mL), and the solution was filtered, then cooled, and treated with concentrated $NH_4OH$ to pH 7 to cause solid to precipitate. The mixture was kept at 0°–5° C. overnight before the solid was collected and washed with cold $H_2O$. This crude material was applied to a silica gel column and eluted with $CHCl_3$—MeOH (7:1). Evaporation of the product fractions afforded the aldehyde compound 2,4-diamino-5-propylpyrido[2,3-d]pyrimidine-6-carboxaldehyde; yield 8% (41 mg).

Anal. Calcd. for $C_{11}H_{13}N_5O \cdot 0.2H_2O$: C, 56.26; H, 5.75; N, 29.82. Found: C, 56.26; H, 5.70, N, 29.72. MS, m/e 232, MH+; UV, ($\epsilon \times 10^{-3}$) in 0.1N HCl, 235 (22.9), 257 (19.5), 316 (9.15); pH 7 buffer, 234 (15.7), 265 (17.4), 318 (11.0), 346 (12.2); in 0.1N NaOH, 234 (17.5), 265 (16.6), 347 (12.8); 1H NMR ($Me_2SO-d_6$), δ 0.92 (t, 3, $CH_3$), 1.55 (sext, 2, $CH_2\underline{CH_2}CH_3$), 3.46 (t, 2, $\underline{CH_2}CH_2CH_3$), 6.84 (br s, 2, $NH_2$), 7.30 (s, 2, $NH_2$), 8.88 (s, 1, $C_7$—H), 11.0 (s, 1, CHO).

2,4-Diamino-5-propylpyrido[2,3-d] pyrimidine-6-methanol (III-1, where $R_1$ is propyl)

2,4-Diamino-5-propylpyrido [2,3-d]pyrimidine-6-carboxaldehyde (95 mg, 0.41 mmol) was stirred with MeOH (20 mL), and the near-solution was treated with 3 portions of $NaBH_4$ (17 mg total, 0.45 mmol) added at 15-min intervals. Complete solution occurred after the first addition of $NaBH_4$. The solution was left at 20°–25° C. for 1 hour. The solution was treated with $H_2O$ (1 mL), neutralized to pH 7 with glacial AcOH, and evaporated to near dryness. Solid residue was stirred with a little cold $H_2O$ (~1 mL), collected, and dried to give a first crop of 6-hydroxymethyl compound (III-1, where $R_1$ is propyl); yield 31% (30 mg). The filtrate from this compound was evaporated to dryness, and the residue was extracted several times with boiling EtOAc to provide additional product (80 mg).

MS, m/e 234, MH+ for $C_{11}H_{15}N_5O$: 1H NMR ($Me_2SO-d_6$), δ 0.96 (t, 3, $CH_3$), 1.56 (sext, 2, $CH_2\underline{CH_2}CH_3$), 3.06 (t, 2, $\underline{CH_2}CH_2CH_3$), 4.52 (s, 2, $CH_2OH$), 6.22 (s, 2, $NH_2$), 6.90 (s, 2, $NH_2$), 8.48 (s, 1, $C_7$—H).

6-(Bromomethyl)-2,4-diamino-5-propylpyrido [2,3-d]pyrimidine (III-2, where $R_1$ propyl)

The hydroxymethyl compound 2,4-diamino-5-propylpyrido[2,3-d]pyrimidine-6-methanol (III-1) was treated with dry HBr in AcOH as reported for 6-(bromomethyl)-2,4-diaminopyrido [2,3-d]pyrimidine (III-2, where $R_1$ is H). Addition of $Et_2O$ caused precipitation of yellow solid which was collected with the aid of $Et_2O$ and dried in vacuo to afford the HBr salt of the product (III-3).

MS m/e 296 and 298, MH+ for $C_{11}H_{14}BrN_5$, but with higher mass peaks present. The 1H NMR spectrum of the product mixture showed expected singlets due to the $CH_2Br$ (4.92) and the $C_7$—H (8.78). Relative integral values suggested about 10 mole-percent of the product.

N-[5-[[(2,4-Diamino-5-propylpyrido[2,3-d]pyrimidine-6-yl)methyl]amino]thiophene-2-carbonyl]L-glutamic acid (49)

A mixture of the crude bromomethyl preparation III-2 described above (0.55 g), diethyl N-(5-aminothiophene-2-carbonyl)-L-glutamate (III-3, where $R_2$ is H) (0.40 g, 1.2 mmol) and $CaCO_3$ (160 mg) in $Me_2NAc$ (7 mL) was stirred at 20°–25° C. for 4 days. Insoluble material was removed by filtration, and the filtrate was evaporated to dryness. The residue was chromatographed on silica gel with elution by $CHCl_3$—MeOH (5:1) to give fractions homogeneous in the desired product. Evaporation of the pooled fractions gave the diethyl ester III-4e, N-[5-[[(2,4-diamino-5-propylpyrido [2,3-d]pyrimidine-6-yl)methyl]amino]thiophene- 2-carbonyl]L-glutamic acid (49) as a pale-orange solid (20 mg).

MS m/e 545, MH+ for $C_{25}H_{33}N_7O_5S$.

For ester hydrolysis, this sample was dissolved in 1 N NaOH (0.37 mL), and the solution was kept at 20°–23° C. for 5 h. The solution was clarified (Celite mat), then acidified to pH 3.8–4.0 with 2N HCl. After the mixture had been refrigerated, the solid product compound 49 was collected and dried; yield 6 mg.

MS, m/e 488, MH+ for $C_{21}H_{25}N_7O_5S$.

EXAMPLE 8

Preparation of N-(5-(2-(2,4-Diaminopyrido[2,3-d]pyrimidine-6-yl)ethylthiophene]-2-carbonyl)-L-glutamic Acid (75)

This example illustrates preparation of Preparation of N-[5-(2-(2,4-diaminopyrido[2,3-d]pyrimidine-6-yl) ehtylthiophene)-2-carbonyl]-L-glutamic acid by the procedure illustrated in Reaction Scheme 4, resulting in compound 75, seen in Table 3.

2-Carboxythiophene-5-Acetic Acid Dimethyl Ester (IV-2)

Freshly distilled diisopropylamine (24.6 g, 0.24 mol) in 250 mL of dry tetrahydrofuran (THF) was cooled to 0° C. under argon, then treated dropwise with 98 mL (0.24 mol) of 2.5M BuLi in hexane. After 1 hour, the LDA solution was added dropwise with stirring to a −30° mixture of 15.0 g (0.11 mol) of 5-methylthiophene-2-carboxylic acid (IV-1) in 300 mL of dry THF. The temperature of the resulting red solution was allowed to rise to 0° C. and was maintained at that temperature for another 2 hours. Carbon dioxide was bubbled through the solution to produce a yellow precipitate. The mixture was stirred at ambient temperature for 2 hours and filtered. The yellow filter cake was suspended in 300 mL of MeOH, and the mixture was cooled to 0° C. and treated with 100 mL of MeOH saturated with dry HCl. The mixture was stirred at room temperature for 72 hours, concentrated in vacuo and the residue was partitioned between $Et_2O$ (500 mL) and 250 mL of saturated $NaHCO_3$. The $Et_2O$ extract was washed with $H_2O$ (3×250 mL), dried over $MgSO_4$, and evaporated to leave a dark oil (15 g). Chromatography on flash silica gel (EtOAc-hexane, 1:19) gave 11.4 g of the product IV-2 (51%) as a white, waxy solid.

NMR ($CDCl_3$) δ 7.61 (d, 1H, 3-H); 6.90 (d, 1H,. 4-H); 3.87 (m, 5H, $ArCOOCH_3+CH_2$); 3.82 (s, 3H, $CH_2COOCH_3$); Anal. ($C_9H_{10}O_4S$); Calc: C, 50.5; H, 4.71; Found: C, 50.6; H, 4.79.

5-[1-Carbomethoxy-2-(2,4-diamino[2,3-d]pyrimidine-6-yl) ethyl]thiophene-2-carboxylic Acid Methyl Ester (IV-3)

The sodium derivative of 2-carbomethoxythiophene-5-acetic acid methyl ester (IV-2) (12.0 mmol) was prepared in DMF using NaH (480 mg of 60% dispersion in oil, 12.0 mmol). The mixture was treated with a solution of 6-(bromomethyl)- 2,4-diaminopyrido [2,3-d]pyrimidine III-2 (1.6 g, 4.0 mmol) in 10 mL of DMF at -25° C.. The mixture was kept at −10° C. for one hour and then stirred for one hour at room temperature, followed by neutralization with solid $CO_2$. Silica gel was added followed by evaporation in vacuo. The solid residue was applied to a silica gel column and the product eluted with $CHCl_3$—MeOH (9:1) to afford the product IV-3, in 23% yield (350 mg).

Mass spectrum, m/e 388, MH+ for $C_{17}H_{17}N_5O_4S$.

5-[1-Carboxy-2-(2,4-diamino[2,3-d]pyrimidine-6-yl)ethyl]thiophene-2-carboxylic Acid (IV-4)

The ester IV-3 (350 mg) was hydrolyzed by 4N NaOH (0.5 mL) in dimethylsulfoxide (DMSO) for 20 hours, followed by removal of DMSO at 40° in vacuo. Precipitation of IV-4 from a solution of its Na salt in $H_2O$ by treatment with 1N HCl to pH 4.0 gave a gel-like precipitate. The gel became particulate solid after the mixture had been frozen solid and then allowed to thaw. The solid product IV-4 was collected by filtration; yield 85% (275 mg).

Mass spectrum, m/e 360, MH+ for $C_{15}H_{13}N5O_4S$. Assay by HPLC, >93% purity.

5-[2-(2,4-Diamino[2,3-d]pyrimidine-6-yl)ethyl]thiophene-2-carboxylic Acid (IV-5)

A solution of IV-4 (235 mg, 0.65 mmol) in DMSO (8 mL) was kept at 120–125° C. for 20 min. Removal of DMSO in vacuo (<1 mm, bath to 40° C.) gave the product IV-5, 210 mg.

Mass spectrum, m/e 316, MH+ for $C_{14}H_{13}N_5O_2S$. This material was used directly for conversion to IV-6.

N-[5-[2-(2,4-Diamino[2,3-d]pyrimidine-6-yl)ethyl]thiophene-2-carbonyl]-L-glutamic Acid Diethyl Ester (IV-6)

A stirred mixture of IV-5 (210 mg, 0.66 mmol) in DMF (25 mL) was treated with $Et_3N$ (0.37 mL, 26 mg, 2.64 mmol) followed by i-BuOCOCl (0.09 mL, 92 mg, 0.66 mmol), then stirred at 20°–23° C. for 15 minutes before diethyl L-glutamate HCl (158 mg, 0.66 mmol) was added. Three more additions of i-BuOCOCl (0.33, 0.17, and 0.17 mmol) were made at intervals of 15 minutes, and each was followed 1 minute later by addition of an equimolar amount of diethyl L-glutamate HCl. The course of the conversion was followed by TLC ($CHCl_3$—MeOH, 3: 1), and a chromatogram observed 2 hours after the final addition revealed one major UV-absorbing spot. DMF was then removed (<1 mm, 25°–30° C.). The residue was dissolved in MeOH, and the solution was treated with silica gel (2.0 g of 60–200 mesh). Evaporation gave a dry dispersion of crude product in silica gel which was applied atop a column of silica gel. The column was eluted with $CHCl_3$—MeOH (5:1), and fractions were examined by TLC. Appropriate fractions were combined and evaporated, and the residue was stirred with Et20, then collected by filtration. The yield of diethyl ester (IV-6) was 36% (120 mg).

Mass spectrum, m/e 501, MH+ for $C_{23}H_{28}N_6O_5S$.

N-[5-[2-(2,4-Diamino[2,3-d]pyrimidine-6-yl) thiophene]-2-carbonyl]-L-glutamic Acid (75)

The diethyl ester IV-6 (120 mg) was dissolved in MeOH (10 mL) along with 1N NaOH (0.5 mL). After 2 days at 20°–23° C. in a stoppered flask protected from light, the solution was evaporated in vacuo bath 25° C., to remove MeOH which was replaced with $H_2O$ (10 mL). More 1N NaOH (0.25 mL) was added, and the aqueous solution was left at 20°–23° C. for 2 days before it was treated with 1N HCl (pH 4.0). The precipitated product was collected, washed with $H_2O$, and dried (in vacuo) to afford N-[5-[2-(2,4-diaminopyrido[2,3 -d]pyrimidine-6-yl) ethylthiophene] 2-carbonyl]-L-glutamic acid, compound 75 in 37% yield (43 mg).

MS, m/e 445, MH+. Anal. Calcd for $C_{19}H_{20}N_6O_5S°$ $2H_2O$: C, 47.49; H, 5.03; N, 17.49. Found: C, 47.23; H, 4.81; N, 17.13.

EXAMPLE 9

Preparation of N-[2-[2-(2,4-Diaminopyrido[2,3-d] pyrimidine-6-yl)ethyl-5-pyridyl] carbonyl](5,10-Dideaza-3'-azaaminopterin) L-glutamic Acid (97)

This example illustrates preparation of N-[2-[2-(2,4 -diaminopyrido[2,3-d]pyrimidine-6-yl) ethyl-5-pyridyl]carbonyl]-L-glutamic acid, according to Reaction Scheme 5, resulting in compound 97, seen in Table 3.

3-Carboxypyridine-6-acetic Acid Dimethyl Ester (V-2)

This diester was prepared similarly as compound IV-2 from 6-methylnicotinic acid (V-1) as a yellow solid, mp 56°–57° C..

NMR ($CDCl_3$) δ 9.10 (m, 1H, 2-H); 8.21 (m, 1H, 4-H); 7.33 (m, 1H, 5-H); 3.84 (m, 8H, $CH_2COOCH_3$ and $ArCOOCH_3$); Anal. ($C_{10}H_{11}NO_4$); Calc: C, 57.4; H, 5.30; N, 6.70. Found: C, 57.5; H, 5.33; N, 6.54.

10-Carbomethoxy-4-deoxy-4-amino-5, 10-dideaza-3'-azapteroic Acid Methyl Ester (V-3)

Alkylation of the sodium derivative of 3-carbomethoxy-6-pyridylacetic acid methyl ester (V-2) with compound 6 -(bromomethyl)-2,4-diaminopyrido [2,3-d]pyrimidine III-2, where $R_1$ is hydrogen, to produce compound V-3, was performed as described above in Example 8 for the preparation of compound IV-3. The product V-3 obtained in greater than 90% yield was nearly homogeneous by TLC ($CHCl_3$—MeOH, 5:1) and produced the expected mass spectral peak of m/e 393, MH+ for $C_{18}H_{18}N_6O_4$. Purity assay by HPLC showed the main component to be >86% with respect to UV-absorbing material. The compound V-3 was used as such for conversion to V-4.

10-Carboxy-4-deoxy-4-amino-5, 10-dideaza-3'-azapteroic Acid (V-4)

Ester hydrolysis of compound V-3 was conducted as described in Example 8 for the conversion of compound IV-3 to compound IV-4. The overall yield of compound V-4 was 86% (1.25 g from 1.66 g).

Mass spectrum, m/e 355, MH+ for $C_{16}H_{14}N_6O_4$.

4-Deoxy-4-amino-5,10-dideaza-3'-azapteroic Acid (V-5)

Compound V-4 (1.25 g) was suspended in DMF (30 mL), and the stirred mixture was heated at 75° C. for 20 min. Evolution of $CO_2$ appeared to cease after 10 min although solution did not occur. DMF was removed in vacuo, and the residue was stirred with $H_2O$, collected and dried to give V-5 (0.88 g, ~84% yield).

Mass spectrum, m/e 311, MH+ for $C_{15}H_{14}N_6O_2$.

N-[2-[2-[(2,4-Diaminopyrido[2,3-d]pyrimidine-6-yl) ethyl]-5-pyridyl]carbonyl]-L-glutamic acid (97)

Compound V-5 was coupled with diethyl L-glutamate in the same manner as described for compound IV-6 in Example 8. The yield of pure ester V-6, homogeneous by TLC (CHCl$_3$-MeOH, 5:1; Rf~0.5), was about 18% (215 mg from 740 mg, 2.38 mmol.

Mass spectrum, m/e 496, MH+ for $C_{24}H_{29}N_7O_5$.

Hydrolysis of the ester groups of the product V-6 (175 mg, 0.353 mmol) was the same as described in Example 8 and led to pure N-[2-[2-[(2,4-diaminopyrido [2,3-d]pyrimidine-6 -yl) ethyl]-5-pyridyl]carbonyl]-L-glutamic acid, compound 97 in 77% yield (119 mg).

Mass spectrum, m/e 440; 1H NMR d 1.95, 2.08 (two m, 2, glu-3-CH$_2$), 2.34 (t, 2, CH$_2$CO), 3.06 (m, 2, C-9H$_2$ or C-10 -H$_2$), 3.17 (m, 2, C-9 or C-10), 4.38 (m, 1, CHNH), 6.85 (s, 2, NH$_2$), 7.36 (d, 1, pyridyl-3-H), 7.84 (s, 2, NH$_2$), 8.12 (m, 1, pyridyl-4-H), 8.37 (d, 1, C5-H), 8.54 (d, 1, C$_7$—H), 8.68 (d, 1, CONH), 8.97 (d, 1, pyridyl-6-H). Anal. Calcd for $C_{20}H_{21}N_7O_5$ 3H$_2$O: C, 48.68; H, 5.51; N, 19.87. Found: C, 48.45; H, 5.55; N, 19.75.

EXAMPLE 10

Preparation of
5-Methyl-5,10-Dideaza-3'-Azaaminopterin (115)

This example illustrates preparation of N-[2-[2-[(2,4 -diamino-5-methylpyrido [2,3-d]pyrimidine-6-yl-ethyl]-5 -pyridyl]carbonyl]-L-glutamic acid (5-methyl-5,10-dideaza-3'-azaaminopterin), by the procedure illustrated in reaction Scheme 5, compound 115 in Table 3.

10-Carbomethoxy-4-deoxy-4-amino-5-methyl-5,10-dideaza-3'-azapteroic Acid Methyl Ester (V-3, Where R$_1$ is CH$_3$)

NaH (480 mg of 60% in oil, 12.0 mmol) was suspended in DMF (12 mL), and the mixture was chilled to 0° C. then treated with a solution of 3-carbomethoxy-6-pyridylacetic acid methyl ester (V-2, 2.50 g, 12.0 mmol) in DMF (12 mL). After 0.5 hour at 0° C., the stirred mixture was chilled to −25° C., and treated with a solution of 6-bromomethyl-2,4 -diamino-5-methylpyrido[2,3-d]pyrimidine (III-2, where R$_1$ is CH$_3$) in 1.7 HBr; 0.5 AcOH (1.71 g, 3.92 mmol) in DMF (12 mL), then allowed to warm to -10° C.. After 1 hour at near −10° C. the solution was allowed to reach the ambient temperature. After 1 hour at 20°–23° C., the mixture was neutralized by the addition of small amount of solid CO$_2$. Addition of silica gel (7.5 g of 60–200 mesh) followed, and the resulting mixture was evaporated to dryness (<1 mm, bath to 40° C.) to give a dispersion of crude product in silica gel which was applied to a column of silica gel. Elution by CHCl$_3$—MeOH (9:1) led to homogeneous fractions 8 according to TLC (CHCl$_3$—MeOH, 3:1; Rf ~0.6). Evaporation of the combined fractions gave product V-3, where R$_1$ is CH$_3$, in 43% yield (668 mg). Mass spectrum, m/e 397, MH+ for $C_{19}H_{20}N_6O_4$.

10-Carboxy-4-deoxy-4-amino-5-methyl-5,10-dideaza-3'-azapteroic Acid (V-4, where R$_1$ is CH$_3$)

A suspension of compound V-3, where R$_1$ is CH$_3$ (668 mg, 1.69 mmol) in DMSO was treated with 4N NaOH (1.0 mL). The resulting clear solution was kept under N$_2$ in a stoppered flask protected from light for 20 hours. After the solvent had been removed by short-path distillation in vacuo (<1 mm, bath to 40° C.), the residue was dissolved in H$_2$O (30 mL), and the filtered solution was acidified to pH 5 using glacial AcOH. The mixture was kept several hours in a refrigerator before the solid was collected, washed with H$_2$O, and dried in vacuo (over P$_2$O$_5$). This material was found by HPLC assay and by mass spectrometry to be a mixture consisting of 88% compound V-4, where R$_1$ is CH$_3$ (m/e 369, MH+ for $C_{17}H_{16}N_6O_4$) and 12% of the sequential product V-5, where R$_1$ is CH$_3$ (m/e 325, MH+ for $C_{16}H_{16}N_6O_2$). The weight of the mixture (594 mg) corresponds to conversion of 97%.

4-Amino-4-deoxy-5-methyl-5,10-dideaza-3'-azapteroic Acid (V-5, where R$_1$ is CH$_3$)

The above material V-4, (594 mg) was suspended in DMF (15 mL), and the stirred mixture was kept at 60°–65° C. for 12 min. Decarboxylation was slow at this temperature, and the temperature of the bath was raised to 80°–85° C. Heating was continued 15 min longer. To ensure complete reaction, DMF was removed in vacuo and replaced with DMSO. The resulting clear solution was kept at 60°–65° C. for 15 min, then examined by HPLC showing complete decarboxylation. DMSO was removed in vacuo, and the product was precipitated from a clarified (Norit, Celite) aqueous solution of its Na salt by addition of AcOH to pH 5; yield was 77% (443 mg) of compound V-5, where R$_1$ is CH$_3$.

Mass spectrum, m/e 325, MH+. Anal. Calcd for $C_{16}H_{16}N_6O_2$: C, 54.69; H, 5.45; N, 23.92. Found: C, 54.77; H, 5.13; N, 4.41.

N-[2-[2-[(2,4-Diamino-5-methylpyrido[2,3-d]pyrimidine-6-yl) ethyl]-5-pyridyl]carbonyl]-L-glutamic Acid Diethyl Ester (V-6, where R$_1$ is CH$_3$)

A stirred mixture of V-5, where R$_1$ is CH$_3$ (382 mg, 1.09 mmol) in DMF (40 mL) was treated with Et$_3$N (0.61 mL, 0.44 mg, 44 mmol) followed by i-BuOCOCl (0.14 mL, 0.15 g, 1.08 mmol), then stirred at 20°–23° C. for 15 min before diethyl L-glutamate HCl (261 mg, 1.09 mmol) was added. Three more additions of i-BuOCOCl (0.55, 0.27, and 0.27 mmol) were made at intervals of 15 minutes. Each addition was followed 1 minute later by an equimolar amount of diethyl L-glutamate HCl. The course of the conversion was followed by TLC (CHCl$_3$—MeOH, 3:1), and a chromatogram observed 2 hours after the final addition revealed one major UV-absorbing spot. DMF was then removed (<1 mm, 25°–30° C.). The residue was dissolved in MeOH, and the solution was treated with silica gel (2.0 g of 60–200 mesh). Evaporation gave a dry dispersion of crude product in silica gel which was applied to a top of a silica gel column (~300 mL of 230-400 mesh). The column was eluted with CHCl$_3$—MeOH (5:1), and fractions were examined by TLC. Appropriate fractions were combined and evaporated, and the residue was stirred with Et$_2$O, then collected by filtration. The air-dried sample was stirred with H$_2$O. The H$_2$O insoluble solid was dried to give the diethyl ester compound V-6, where R$_1$ is CH$_3$ (281 mg, 47%).

Mass spectrum, m/e 510, MH+. Anal. Calcd for $C_{25}H_{31}N_7O_5$° 2H$_2$O: C, 55.04; H, 6.47; N, 17.97. Found: C, 55.01; H, 6.23; N, 17.88.

N-[2-[2-[(2,4-Diamino-5-methylpyrido[2,3-d] pyrimidine-6-yl)ethyl]-5-pyridyl]carbonyl]-L-glutamic Acid (115)

The ester (261 mg, 0.478 mmol) was dissolved in MeOH (20 mL) containing IN NaOH (1.1 mL). After 2 days at 20°–23° C. in a stoppered flask protected from light, the solution was evaporated in vacuo, bath 25° C. to remove MeOH which was replaced with H$_2$O (20 mL). More 1N NaOH (0.5 mL) was added, and the aqueous solution was left at 20°–23° C. for 2 days longer before it was treated with 1N HCl to pH 4.0 to cause precipitation. The product was collected, washed with H$_2$O, and dried to give compound 115 in 88% yield (204 mg).

Mass spectrum, m/e 454, MH+; UV (ε×10-3) 0.1N HCl, 228 (38.6), 270 (17.6), 319 (7.96); pH 7, 233 (38.5), 268 (16.6), 334 (6.01); 0.1N NaOH, 233 (37.4), 269 (18.1), 345 (6.72); 1H NMR (Me$_2$SO—d6) δ 1.95, 2.06 (two m, 2, glu-3 -CH$_2$), 2.34 (t, 2, CH$_2$CO), 2.68 (s, 3, CH$_3$), 3.06 (m, 4, -CH$_2$CH$_2$), 4.38 (q, 1, CHNH), 6.90 (s, 2, NH$_2$), 7.34 (m, 3, NH$_2$ overlapping pyridyl-3-H), 8.10 (m, 1, pyridyl-4-H), 8.30 (s, 1, C$_7$—H), 8.64 (d, 1, CONH), 8.96 (d, 1, pyridyl-6-H). Anal. Calcd for C$_{21}$H$_{28}$N$_7$O$_5$° 1.6H$_2$O: C, 52.30; H, 5.48; N, 20.33. Found: C, 52.19; H, 5.34; N, 20.45.

EXAMPLE 11

Preparation of 10-Allyl-4-Deoxy-4-Amino-10 Deazapteroic Acid (VII-5a)

This example illustrates preparation of 10-allyl-4 -deoxy-4-amino-10 deazapteroic acid used for preparation of 10-alkenyl and 10-alkynyl 10-deazaaminopterins.

α-Allyhomoterephthalic Acid Dimethyl Ester (VII-2, where R$_2$ is allyl)

A mixture of 35% potassium hydride oil suspension (6.04 g, 35% w/w/, 53 mmols of potassium hydride) in 240 ml of sieve dried tetrahydrofuran was cooled to 0° C. The cold mixture was treated with homoterephthalic acid dimethyl ester (10.0 g, 48 mmols). The mixture was stirred at 0° C. for 1 hour. Allyl bromide (6.41 g, 53 mmols) was added and the mixture stirred at 0° C. for 30 min., then at room temperature for 16 hours. The resulting mixture was treated with 4.8 ml of 50% acetic acid, then poured into 480 ml of water. The mixture was extracted with either (2× 250 ml). The ether extracts were combined, dried over magnesium sulfate, and concentrated to a brown oil. Chromatography on 250 g of flash silica gel (10% ether in hexane eluent) gave the product VII-2 as a pale yellow oil, 10.5 g (89% yield).

$^1$H NMR (CDCl$_3$): δ =7.69 (q, 4H, Ar); 5.64 (m, 1H, CH=CH$_2$); 5.09 (m, 2H, CH$_2$=CH). 3.80 (m, 7H, 2× CH$_3$O ♦ ArCH); 2.75 (m, 2H, CH$_2$CHAr).

10-Allyl-10-carbomethoxy-4-deoxy-4-amino-10 -Deazapteroic Acid Methyl Ester (VII-3a)

A mixture of potassium hydride in oil (2.43 g, 35% w/w/, 21.2 mmols) in dry dimethylformamide (25 ml) was cooled to −5° C. The cold mixture was treated, dropwise, with a solution of α-allylhomoterephthalic acid dimethyl ester (VII-2) (5.25 g, 21.2 mmols) in dry dimethylformamide (25 ml), then stirred at 0° C. for 45 minutes. After cooling to −20° C. a solution of 2,4-diamino-6-bromomethylpteridine hydrobromide and 0.2 isopropanol (2.45 g, 7.06 mmols) in dry dimethylformamide (40 ml) was added dropwise, maintaining a −20° C. reaction temperature. The temperature was allowed to rise to 20° C. and was stirred for 2.5 hours. The reaction was then adjusted to pH 7 by addition of solid carbon dioxide. Concentration under high vacuum gave a residue which was dissolved in chloroform. This solution was washed with water, dried, and concentrated. The residue was washed with ether and dried in vacuo giving 2.2 g of product VII-3a (74% yield). Thin layer chromatography (10% methanol in chloroform on silica gel plates) showed a single spot, Rf 0.4.

Mass spectrum m/e 423 (M+H). $^1$H NMR (CDCl$_3$): 8.45 (2, 1H, 7—H); 8.03 (d, 2H, C$_6$H$_4$); 7.37 (d, 2H, C$_6$H$_4$); 5.50 (m, CH=CH$_2$); 4.95 (m, 2H, CH$_2$=CH); 3.90 (s, 3H, ArCOOCH$_3$); 3.60 (m, 5H, C-10 COOOCH$_3$—C—9 CH$_2$); 2.83 (m, 2H, CH$_2$CH=CH$_2$).

10-Allyl-10-carboxy-4-deoxy-4-amino-10-deazapteroic Acid (VII-4a).

A solution of the dimethyl ester VII-3a (2.0 g, 4.7 mmols) in 2-methoxyethanol (2 ml) was treated first with water (2 ml) and then with 10% sodium hydroxide (2 ml). The solution was stirred at room temperature for 24 hours. The solution was adjusted to pH 6 with acetic acid and concentrated under high vacuum to give a residue which was then dissolved in water (10 ml). Further acidification to pH 3 resulted in a precipitate which was collected, washed with water and dried in vacuo to yield 1.53 g of yellow acid VII-4a (81%). HPLC (25% methanol in 0.1 molar monobasic sodium phosphate pH 6.5, Novapak C$_{18}$ radial compression column) indicated 90% purity.

Mass spectrum m/e 395 (M+H); UV (0.1N NaOH): λmax 255 nm (28,194), 368 (7,444).

10-Allyl-4-deoxy-4-amino-10-deazapteroic Acid (VII-5a)

A solution of the dicarboxylic acid VII-4a (0.26 g) in dry dimethyl sulfoxide (10 ml) was placed in pre-heated 142° C. oil bath for 10 minutes. The solution was cooled to 35° C. and concentrated under high vacuum. The residue was triturated with ether to yield 0.23 g of a tan solid 10 -Allyl-4-deoxy-4-amino-10-deazapteroic Acid (VII-5a) in 99% yield HPLC (Novapak C$_1$ radial compression column, 25% methanol in 0.1 molar monobasic sodium phosphate, pH 6.5) indicated 95% purity.

Mass spectrum: m/e 351 (M+H).

EXAMPLE 12

Preparation of 10-Propargyl-4-Deoxy-4 -Amino-10-Deazapteroic Acid (VII-5b)

This example illustrates preparation of 10-propargyl-4-deoxy-4 amino-10-deazapteroic acid useful for preparation of 5-alkyl, 5-alkenyl, 5-alkynyl-5-deazaminopterins and 5,10 dideazaminopterins wherein A is N.

α-Propargylhomoterephthalic Acid Dimethyl Ester (VII-2, where R$_2$ is propargyl)

A mixture of 35% potassium hydride in oil (6.04 g, 35% w/w, 53 mmols of potassium hydride) in 240 ml of sieve dried tetrahydrofuran was cooled to 0° C. The cold mixture was treated with homoterephthalic acid dimethyl ester (10.0 g, 48 mmols). The mixture was stirred at 0° C. for 1 hour. Propargyl bromide (53 mmols) was added and the mixture stirred at 0° C. for 30 min., then at room temperature for 16 hours. The resulting mixture was treated with 4.8 ml of 50% acetic acid, then poured into 480 ml of water. The mixture was extracted with ether (2×250 ml). The ether extracts were combined, dried over magnesium sulfate, and concentrated to a brown oil. Chromatography on 250 g of flash silica gel (10% ether in hexane eluent) gave the product as a white solid mp 63°–65° C.

Mass spectrum m/e 247 (M+H). IR (Nujol) CmCH, 3268 cm$^{-1}$. $^1$H NMR (CDCL$_3$): δ 8.05 (d, 2H, C$_6$H$_4$); 7.04 (d, 2H, C$_6$H$_4$); 3.91 (s, 3H, ArCOOOCH$_3$); 3.88 (dd, 1H, ArCH); 3.71 (s, 3H, -CHCOOOCH$_3$); 2.95 (ddd, 1H, CH$_2$); 2.64 (dddd, 1H, CH$_2$); 1.96 (dd, 1H, C=CH). Anal. Calcd. for C$_{14}$H$_{14}$)$_4$: C, 68.3; H, 5.73. Found: C, 68.0; H, 5.60.

10-Propargyl-10-carbomethoxy-4-deoxy-4-amino-10-deazapteroic Acid Methyl Ester (VII-3b)

A mixture of potassium hydride (2.43 g, 35% w/w/, 21.2 mmols) in dry dimethylformamide (25 ml) was cooled to −5° C. The cold mixture was treated dropwise, with a solution of propargylhomoterephthalic acid dimethyl ester VII-2, where R$_2$ is propargyl (21.2 mmols), in dry dimethylformamide (25 ml) and then stirred at 0° C. for 45 minutes. After cooling to −20° C., a solution of 2,4-diamino-6-bromomethylpteridine hydrobromide in 0.2 isopropanol (2.45 g, 7.06 mmols) in dry dimethylformamide (40 ml) was added dropwise, maintaining a −20° C. reaction temperature. The temperature was allowed to rise to 20° C. and was stirred for 2.5 hours. The reaction was then adjusted to pH 7 by addition of solid carbon dioxide. Concentration under high vacuum gave a residue VII-3b which was not soluble in common organic solvents. The residue was carried unpurified into the next step. The purity of unpurified product VII-2 was acceptable by thin layer chromatographic analysis. The crude weight recovery of the product VII-2 was 90%.

Mass spectrum m/e 420.

10-Propargyl-10-carboxy-4-deoxy-4-amino-10-deazapteroic Acid (VII-4b)

A solution of the dimethyl ester (VII-3b) (4.7 mmols) in 2-methoxyethanol (2 ml) was treated with water (2 ml) then with 10% sodium hydroxide (2 ml). The solution was stirred at room temperature for 24 hours. The solution was adjusted to pH 6 with acetic acid and concentrated under high vacuum to give a residue which was then dissolved in water (10 ml). Further acidification to pH 6 resulted in a precipitate which was collected, washed with water and dried in vacuo. HPLC analysis indicated 92% purity after re-precipitation of the product from basic solution. The product VII-4b was obtained as a white solid in 75% yield.

Mass spectrum m/e 680 (M—H as the TMS$_4$ derivative).

10-Propargyl-4-deoxy-4-amino-10-deazapteroic Acid (VII-5b)

Three decarboxylations of VII-4b were conducted on 86, 86, and 55 mg of material. In each use of the reaction aliquot was dissolved in 3 ml of dimethyl sulfoxide and immersed for a period of five minutes in an oil bath preheated to 123° C. The reactions were combined and the solvent removed in high vacuum. The residue was precipitated twice from dilute ammonium hydroxide solution by addition of acetic acid. HPLC analysis indicated 85% purity with no impurity exceeding 4%. The product VII-4b was a tan solid (29% yield).

Mass spectrum: m/e 564 (M+H as the TMS$_3$ derivative).

EXAMPLE 13

Preparation of 4-Deoxy-4-Amino-5,10-Dideazapteroic Acid (VII-5c)

This example illustrates preparation of 4-deoxy-4-amino-5,10-dideazapteroic acid (VII-5c) useful for preparation of 5,10-dideazaaminopterins.

10-Carbomethoxy-4-deoxy-4-amino-5,10-dideazapteroic acid ethyl ester (VII-3c)

NaH (4.80 mg of 60% dispersion in oil, 12.0 mmol) was suspended in DMF (9 ml), and the mixture was chilled to 0° C., then treated with a solution of homoterephtalic acid dimethyl ester VII-2, where R$_2$is H (2.5 g, 12 mmol) in DMF (9 ml) After 0 5 hours at 0° C. the stirred mixture was chilled to −25° C., treated with a solution of VII-1 where Y is CH, Z is N, and B is Br. (1.25 g, 3 mmol) in DMF (9 ml), and allowed to warm to −10° C. After 2.5 hours at −10°±5° C., the pH was adjusted to 7.0 by using small pieces of solid CO$_2$. The solvent was removed in vacuo, and the residue was suspended in H$_2$O (100 ml) and CHCl$_3$ (375 ml). The aqueous layer was then extracted twice with CHCl$_3$ (375 ml each). The CHCl$_3$ phases were pooled, dried over Na$_2$SO$_4$, and evaporated. The residue was dissolved in CHCl$_3$—MeOH (7:1) and applied to a column of silica gel in CHCl$_3$—MeOH, 7:1. The column was eluted with the same solvent system. Homogenous fractions were pooled, evaporated, and dried to afford a light yellow solid product VII-3c (611 mg, 54% yield). Homogeneous on TLC (Rf=0.44; CHCl$_3$—MeOH, 7:1). MS, m/e 382, (M+H)$^+$.

10-Carboxy-4-deoxy-4-amino-5,10-dideazapteroic acid (VII-4c)

Compound VII-3c (5.50 mg, 1.44 mmol) in DMSO (25 ml) was treated with 1N NaOH (3.5 ml). The reaction flask was flushed with N$_2$, and the mixture was stirred at 20°–25° C. for 24 hours. After the solvent had been removed by short-path distillation in vacuo (bath to 40° C.), the residue was dissolved in H$_2$O (30 ml) and the filtered solution was acidified by using glacial AcOH to pH 5.0. The resulting gel was frozen (dry ice acetone bath), then thawed (in a refrigerator at 3° C.), leaving a particulate solid VII-4c, that was collected, washed with H$_2$O, and dried in vacuo (25° C., P$_2$O$_5$), yielding 442 mg (82% yield).

MS, m/e 354 (M+H)$^+$.

Anal. Calcd. for C$_{17}$H$_{15}$N$_5$O$_4$·1.25 H$_2$O: C, 54.3; H, 4.69; N, 18.6. Found: C, 54.2; H, 4.41; N, 18.6.

4-Deoxy-4-amino-5,10-dideazapteroic Acid (VII-5c)

Progress of the decarboxylation of VII-4c (384 mg, 1.08 mmol) in dry DMSO (15–20 ml) under N$_2$ at 160°–165° C. was monitored by CO$_2$ evaluation, which stopped after 20 min. The DMSO was removed by short-path distillation in vacuo (bath to 40° C.), and the residue was stirred with H$_2$O, collected, and dried in vacuo (25° C., P$_2$O$_5$). Mass spectral analysis indicated the crude product to consist of the desired compound VII-5c and a contaminant of molecular weight 369. The contaminant proved to be insoluble in 1N NaOH and was removed by filtration after the crude product mixture had been stirred with sufficient 1 NaOH to dissolve compound VII-5c. The product was then precipitated by acidification to pH 5.0–5.5 by adding 1N HCl. The resulting mixture gelled, but after being frozen and then allowed to thaw slowly, the precipitate changed to particulate mater and was collected, washed with $H_2O$, and dried in vacuo (25° C., $P_2O_5$) to give product VII-5c in 72% yield (253 mg).

MS: m/e 310, $(M+H)^+$. Anal. Calcd. for $C_{16}H_{15}N_5O_2 \cdot H_2O$: C, 58.7; H, 4.93; N, 21.4. Found: C, 58.3; H, 4.76; N, 21.0.

EXAMPLE 14

Preparation of 5-(β-2,4-Diamino-6-pteridinylethylthiophene-2-Carboxylic Acid (VII-5d)

This example illustrates preparation of 5-(β-2,4-diamino-6-pteridinylethylthiophene-2-carboxylic acid (VII- 5d) useful for preparation of 10-deazaminopterins.

Methyl-5-(α-Carbomethoxy-β-2,4-diamino-6-pteridinyl) ethylthiophene-2-carboxylate (VII-3d)

A suspension of 50% sodium hydride in oil (0.84 g, 17.5 mmol of sodium hydride) in 15 ml of dry dimethyl formamide was cooled to 0° C. A solution of the dimethyl ester of 2-carboxymethylthiophene-5-acetic acid (IV-2) (3.73 g, 17.4 mmol) in 15 ml of dry dimethyl formamide was added dropwise. The resulting mixture was stirred at 0° C. for 1 hour and then cooled to −30° C. and treated with a solution of 2,4-diamino-6-bromomethyl-pteridine hydrobromide (16.1 mmol) in 40 ml 9 of dry dimethyl formamide. The resulting mixture was stirred for 2.5 hours while rising to room temperature, then neutralized (pH 7.5) by adding solid carbon dioxide. The mixture was concentrated under high vacuum, and the residue was washed with ether, then water, and dried under high vacuum to give the product VII-3d as a yellow solid (1.98 g, 88%).

MS m/e 389 (M+H); NMR ($d_6$ DMSO) δ 8.58 (s, 1H, $C_7$—H); 7.60 (m, 3H, $C_3'$—H+$NH_2$); 7.12 (d, 1H, $C_4'$—H); 6.61 (broad s, 2H, $NH_2$); 4.9 (t, 1H, $C_{10}$—H); 3.75 (s, 3H, $C_2'$-$COOCH_3$); 3.63 (m, 5H, $C_{10}$—$COOCH_3$+$C_9$—$H_2$).

5-(α-Carboxy-β-2,4-diaminopteridinyl)ethylthiophene-2-carboxylic Acid (VII-4d)

A solution of the diester VII-3d (1.96 g, 5.05 mmol) in 30 ml of 2-methoxyethanol, water, and 30 ml of 2.5N NaOH was stirred for 1.5 hours. The mixture was filtered, and the filtrate was neutralized to pH 7 with HOAc and concentrated under high vacuum. The residue was suspended in water (30 ml) and adjusted with HOAc to pH 5 to produce a precipitate. Filtration gave a tan solid that was digested in 95% EtOH and filtered to give a tan solid that was washed with $Et_2O$ and dried in vacuo, yielding 1.31 g (77%) of product VII-4d; HPLC showed 92.2% purity.

NMR ($d_6$DMSO) δ 8.51 (s, 1H, $C_7$—H); 7.55 (broad s, 2H, $NH_2$); 7.17 (d, 1H, 3'—H); 6.81 (d, 1H, 4'—H); 6.55 (broad s, 2H, $NH_2$); 4.40 (t, 1H, $C_{10}$—H); 3.15 (m, 2H, $C_9$—$H_2$).

5-(β-2,4-Diamino-6-pteridinylethylthiophene-2-carboxylic Acid (VII-5d)

A solution of the dicarboxylic acid VII-4d (1.31 g, 3.64 mmol) in argon purged DMSO was placed in a 135° C. oil batch for 45 min. The solution was then concentrated under high vacuum to a residue that was digested in $Et_2O$ (50 ml). Filtration yielded a brown solid that was washed with ether and dried in vacuo to give 1.31 g of crude product. The material was suspended in water (75 ml) and treated dropwise with 1.5N $NH_4OH$ to pH 12. Insoluble material was removed by filtration and the filtrate adjusted to pH 5 with HOAc to give a precipitate. Filtration gave a brown solid that was washed with $H_2O$ and dried in vacuo, yielding 0.97 g product (84 %).

UV (0.1N NaOH) 257 nm (e25, 305), 372 (6,491); Anal. ($C_{13}H_{12}N_6O_2S \cdot H_2O$). Calc. C, 46.7; H, 4.22; N, 25.1. Found: c, 46.8; H, 4.01, N. 24.8.

EXAMPLE 15

Preparation of 10-Methyl-4-Deoxy-4-Amino-8,10-Dideazapteroic Acid (VII-5e)

This example illustrates preparation of 10-methyl-4-deoxy-4-amino-8,10-dideazapteroic acid useful for preparation of 8,10-dideazaaminopterins.

α-Methylhomoterphthalic Acid Dimethyl Ester (VI-2, where $R_2$ is $CH_3$)

A mixture of 35% potassium hydride in oil (6.04 g, equivalent to 2.11 g, 53 mmol of potassium hydride) in 240 ml of sieve dried tetrahydrofuran was cooled to 0° C. The cold mixture was treated with homoterephthalic acid dimethyl ester (10.0 g, 48 mmol). The mixture was stirred at 0° C. for 1 hour. Methyl iodide (7.51 g, 53 mmol) was added and the mixture stirred at 0° C. for 30 min, then at room temperature for 16 hours. The resulting mixture was treated with 4.8 ml of 50% acetic acid, then poured into 480 ml of water. The mixture was extracted with ether (2×250 ml). The ether extracts were combined, dried on magnesium sulfate, and concentrated to a brown oil, 15.67 g. Chromatography on 250 g of flash silica gel (10% ether in hexanes eluent) gave the product VII-2 as a pale yellow oil, 7.24 g (67.9% theory).

NMR ($CDCl_3$): δ=7.56 (q, 4H, Ar); 2.78 (m, 7H, 2×$CH_3O$+ArCH); 1.49 (d, 3 H, $CH_3CH$).

10-Methyl-10-carbomethoxy-4-deoxy-4-amino-8,10-dideazapteroic Acid Methyl Ester (VII-3e)

Potassium hydride (3.0 g of 35%, equivalent to 26.2 mmol hydride) in dry dimethyl formamide (19 ml) was cooled to 0° C. To the cold suspension was added α-methylhomoterephthalic acid dimethyl ester VII-2 above (5.8 g, 26.2 mmol) in dry dimethylformamide (20 ml). The yellow-orange mixture was stirred an additional 30 min at 0° C. The reaction mixture was then cooled to -25° C. and 6-bromomethyl-2,4-diamino-8-deazapteridine hydrobromide (2.8 g, 8.3 mmol) in dry dimethylformamide (40 ml) was added dropwise. The temperature was allowed to rise to −10° C. After 2.5 hours, the reaction was adjusted to pH 7 by adding solid carbon dioxide. The mixture was concentrated under high vacuum and the residue shaken in 100 ml of chloroform and water. The organic layer was separated, and the aqueous was again extracted with 50 ml of chloroform. The organic layer was separated, and the aqueous was again extracted with 50 ml of chloroform. The organics were combined, dried on magnesium sulfate, and concentrated. Chromatography of the residue on flash silica gel (chloroform, then 5% methanol in chloroform, then 10% methanol in chloroform) gave 1.5 g of product VII-3e (44%), which was homogeneous by thin-layer chromatography, $R_f$=0.4.

10-Methyl-10-carboxy-4-deoxy-4-amino-8,10-dideazapteroic Acid (VII-4e)

10-Methyl-10-carbomethoxy-4-deoxy-4-amino-8-dezapteroic acid methyl ester (1.5 g, 3.8 mmol) in 2-methoxyethanol (15.5 ml) was treated with 10% sodium hydroxide (15.5 ml), then with water (15.5 ml). The mixture was stirred at room temperature for 24 hours. The pH was adjusted with 4N hydrochloric acid to pH 4. Filtration gave a white solid that was washed with water. After drying in vacuo at 50° C., 1.0 g of VII-4e was obtained as a white solid (71.7%). HPLC showed 96.2% purity.

10-Methyl-4-deoxy-4-amino-8,10-dideazapteroic Acid (VII-5e)

10-Methyl-10-carboxy-4-deoxy-4-amino-8,10 -dideazapteroic acid (VII-4e) (0.92 g, 2.5 mmol) in dry, argon purged dimethyl sulfoxide (20 ml) was warmed in a 180° C. oil bath for 10 min. The mixture was then concentrated under high vacuum. The residue was washed with water and dried in vacuo at 55° C. yielding 0.76 g of product 10-methyl-4-deoxy-4-amino-8,10-dideazapteroic Acid VII-5e(94.1% theory). HPLC showed 97% purity.

NMR ($d_6$—DMSO): $\delta$=7.83 (m, 2H, $C_6H_4$); 7.35 (M, 6h, $C_6H_4$); 7.35 (m, 6H, $C_6H_4$+7—H+8—H+$NH_2$); 6.27 (br s, 2H, $NH_2$); 3.50 (m, 2H, 9—$_2$); 3.07 (m, 1H, 10—H); 1.23 (d, 3H, 10—$CH_3$).

EXAMPLE 16

Capsule Formulation

This example illustrates preparation of compounds of the current invention in a capsule form.

| Capsule Composition | mg/Capsule |
| --- | --- |
| Active Ingredient | 250 |
| Lactose | 150 |

Active ingredient is selected from the group of compounds comprising 5-deazaminopterins or 5,10-dideazaminopterins.

The appropriate deazaaminopterin compound and lactose are passed through a sieve and the powders are well mixed together before filling into hard gelatin capsules of suitable size, so that each capsule contains 400 mg of mixed powders.

Using the same procedure, all other compounds diazaaminopterins are formulated as capsules.

EXAMPLE 17

Suppositories Formulations

This example illustrates preparation of compounds of the current invention as suppositories.

| Composition | mg/suppository |
| --- | --- |
| Active Ingredient | 50 |
| Oil of theobroma | 950 |

Active ingredient as in Example 16 is powdered and passed through a sieve and triturated with molten oil of theobroma at 45° C. to form a smooth suspension.

The mixture is well stirred and poured into molds, each of nominal 1 g capacity, to produce suppositories.

Using the same procedure, all other deazaaminopterins are formulated as suppositories.

EXAMPLE 18

Cachets

This example illustrates formulation of compounds of the current invention into cachets.

| Composition | mg/Cachet |
| --- | --- |
| Active Ingredient | 100 |
| Lactose | 400 |

The active ingredient as in Example 16 is passed through a mesh sieve, mixed with lactose previously sieved and fitted into cachets of suitable size so that each contains 500 mg. of mixture.

Using the same procedure, all other diazaaminopterins are formulated as cachets.

EXAMPLE 19

Injectables

This example illustrates a preparation of compounds of the current invention in injectable forms.

| Composition Intramuscular injection | mg/Injection |
| --- | --- |
| Active Ingredient | 10 |
| Sodium carboxymethylcellulose viscosity) | 2.0 |
| Methyl parahydroxybenzoate | 1.5 |
| Propyl parahydroxylbenzoate | 0.2 |
| Water for injection to 1.0 ml | |

Other injection forms such as intraperitoneal, intravenous, subcutaneous, etc., are prepared similarly.

The compound of the invention and the other excipients, listed above, were dissolved in a sterile solution in an aqueous carrier system. Using the same procedure, 10-alkynyl, all other compounds are formulated as injectables.

EXAMPLE 20

In Vivo Biology Of Type II Collagen Arthritis And Methotrexate Treatment Using 5-Deazaaminopterin Compounds The following data illustrate administration to mice of several 5-deazaaminopterin compounds of the invention and methotrexate in the evaluation of anti-inflammatory activity. The data are presented as two separate observations, the visually observed presence of inflammation in the mouse, and the caliper-measured degree of swelling of the rear paws of the mouse.

The efficacy evaluation used a mouse model of inflammatory disease that occurs in response to an antigenic challenge with Type II collagen, according to methods described in *Nature*, 283:666–668 (1980).

The fundamental aspects of the model allow it to serve as a representative presentation of human disease. The parallels between the known aspects of the mouse model and rheumatoid arthritis include a humoral response in which antibodies are produced to an antigen that is present in the joint tissue and the antigenic challenge is accompanied by cell-mediated aspects of immunity. The resultant inflammation of the joint tissue yields facets of periostitis, synovial lining hyperplasia, degradation of bone and cartilage and pannus and new bone formation.

The basic elements of the model included the immunization of DBA/1 mice with a suspension of fetal bovine Type II collagen (1 mg/ml) prepared in complete Freund's adjuvant. The primary injection was given using 0.1 ml of the collagen emulsion giving a total of 0.1 mg of Type II collagen per mouse. The animals were then given a booster injection of Type II collagen (100 µg in 0.01M acetic acid) on day 21 by intraperitoneal injection.

The results of the in vivo testing of methotrexate showed that using prophylactic regimens in which drug was begun two days prior to administration of antigen (Type II collagen) was more effective than starting drug at day 19, two days prior to the first and only boost with Type II collagen. Typically, in this model the untreated positive control animals have an incidence of arthritis ranging from 90 to 100% of injected animals at day 44.

Test compounds were administered to each animal using a treatment regimen beginning two days prior (Day -2) to the initial immunization with type II collagen. Subsequent drug treatment was administered according to exact body weight (0.1 cc/10 g) using sterile 2% sodium bicarbonate as the vehicle for intra-peritoneal injection. Each drug was tested over a concentration range that began at 9, 6, 3 and 1.50 mg. Depending on apparent drug efficacy, the concentrations for further testing were adjusted upward (12 mg/kg) or downwards (0.75 mg/kg) to complete dose range studies. Each drug dose was tested using 8 animals from statistical power calculations. This number of animals provided sufficiently accurate measurements for intergroup statistical analysis using Student two sample t-test for paw swelling.

The effect of methotrexate and test compounds on the extent of inflammation was determined by direct analysis of paw swelling using caliper measurements. The results are presented in Table 4, and show a direct correlation between the decrease in the number of animals having disease and a decrease in the extent of inflammation, as determined by paw swelling.

TABLE 4

Antiarthritic Activity of 5-Deazaminopterins

| COMPOUND | DOSE (mg/kg) | NUMBER OF MICE EXHIBITING JOINT INFLAMMATION TOTAL NUMBER OF ANIMALS TESTED | | | AVE. THICKNESS OF REAR PAWS (MM) DAYS 30–44 | |
|---|---|---|---|---|---|---|
| | | DAY 30 | DAY 37 | DAY 44 | TREATED[c,d] | UNTREATED[c,d] |
| none | — | 31/43 | 38/43 | 41/43 | — | (2.24–2.98) |
| 5-Me-10-H (5-Me-5-DA) (9a) | 1.5 | 0/8 | 2/8 | 6/8 | (2.18.2.55) | (2.33–2.87) |
| 5-Me-10-Me (5-Me-5-DMTX) (10a) | 1.5 | 1/8 | 4/8 | 5/8 | (2.26–2.44) | (2.33–2.87) |
| 5-Et-10-H (5-Et-5-DA) (16a) | 1.0 | 2/8 | 5/8 | 2/8 | (2.19–2.24) | (2.56–2.98) |
| 5-Et-10-Me (5-Et-5-DMTX) (17a) | 0.75 | 0/7 | 1/7 | 1/7 | (2.20–2.18) | (2.24–2.63) |
| 5-Pr-10-H (5-Pr-5-DA) (21a) | 1.5 | 0/7 | 0/7 | 0/7 | (2.14–2.15) | (2.24–2.63) |
| 5-H-10-Propargyl (10-Prgl-5-DA) (6a) | 12.0 | 3/8 | 2/8 | 6/8 | (2.22–2.37) | (2.34–2.78) |
| 5-Me-10-Propargyl (5-Me-10-Prgl-5-DA) (14a) | 1.5 | 3/8 | 3/8 | 2/8 | (2.29–2.29) | (2.56–2.98) |
| 5-Me-10-Allyl (5-Me-10-Allyl-5-DA) (13a) | 3.0 | 0/8 | 0/8 | 0/8 | (2.12–2.16) | (2.32–2.72) |
| 5,10-Dideazaaaminopterin (1b) | 12.0 | 1/8 | 1/8 | 2/8 | (2.24–2.28) | (2.30–2.58) |
| 10-Me-5,10-Dideazaaminopterin (9b) | 10.0 | 0/5 | 1/5 | 1/5 | (2.23–2.24) | (2.24–2.53) |
| MTX[a] | 9.0 | 1/22 | 1/22 | 6/22 | (2.18–2.34) | (2.24–2.98) |

[a]. Methotrexate (MTX) and untreated controls are composites from multiple runs.
[b]. Visual evidence of inflammation.
[c]. Values in parentheses are 30 day and 44 day measurements vs. equivalent for untreated controls; decrease in inflammation vs. control is most notable at day 44.
[d]. 2.14–2.20 nm represents normal hind paws thickness of age-matched control mice.

It is apparent from the above results that the number of test mice affected was very considerably decreased by administration of the deazaaminopterin compound. The results show the deazaaminopterin compounds on a similar dosage level to be at least as effective as methotrexate, and since methotrexate is accepted as effective drug for treatment of arthritis, the deazaaminopterin compound is, under similar conditions, at least as effective as methotrexate. The potent antiarthritic activity of the deazaaminopterin compounds tested is evident from the results.

In addition to an effectiveness at least as great methotrexate at a similar dosage level, the compounds of the invention have an additional advantage of having a lower-toxicity. Therefore, the dosages higher than methotrexate can be safely administered. The data in Table 5 illustrate lesser cytotoxicity of deazaaminopterins on a human liver cell line (Chang liver) than methotrexate. Results are expressed in terms of the rates of cytotoxic potency versus methotrexate, whose ratio in those terms is 1.00. Thus, the higher the ratio, the lower the toxicity of the compound with respect to methotrexate.

TABLE 5

Ratio Of Cytotoxic Potency Versus Methotrexate For Inhibition Of Human Liver Cell Growth In Culture

| Compound # | | Ratio |
|---|---|---|
| Co | MTX | 1.00 |
| 9a | 5-Me-10-NH | 4.39 |
| 10a | 5-Me-10-NMe | 2.79 |
| 16a | 5-Et-10-NH | 4.50 |
| 17a | 5-Et-10-NMe | 3.18 |
| 21a | 5-Pr-10-NH | 1.78 |
| 25a | 5-Bu-10-NH | 7.20 |
| 14a | 5-Me-10-N-Propargyl | 21.18 |
| 6a | 5-H-10-N-Propargyl | 1.26 |
| 1b | 5,10-Dideazaaminopterin | 2.46 |
| 9b | 10-Me-5,10-Dideazaaminopterin | 2.69 |

Table 5 clearly shows that all deazaaminopterin compounds have lower toxicity than methotrexate.

EXAMPLE 21

In Vivo Biology Of Type II Collagen Arthritis And Methotrexate Treatment Using 5,10-Dideazaaminopterin Compounds The following example illustrates administration to mice of methotrexate and several 5,10-dideazaaminopterin compounds of the invention in the evaluation of anti-inflammatory activity. The data are presented in Table 6 below as two separate observations. The first observation is of a reduction of the visually observed presence of inflammation in the mouse. The second observation is of the visually observed decrease of swelling of the rear paws of the mouse.

The efficacy evaluation uses a mouse model of inflammatory disease that occurs in response to an antigenic challenge with Type II collagen as described above in Example 20.

TABLE 6

Antiarthritic Activity of 5,10-Dideazaminopterins

| COMPOUND | DOSE (MG/KG) | VISUAL OBSERVATION OF REDUCTION OF INFLAMMATION | VISUAL OBSERVATION OF DECREASE OF SWELLING |
|---|---|---|---|
| None | | No | No |
| 5-Me-10-H 5,10-dideaza (9b) | 1.5 | Yes | Yes |
| 5-Me-10-Me 5,10-dideaza (10b) | 1.5 | Yes | Yes |
| 5-Et-10-H 5,10-dideaza (16b) | 1.0 | Yes | Yes |
| 5-Et-10-Me 5,10-dideaza (17b) | 0.75 | Yes | Yes |
| 5-Pr-10-Me 5,10-dideaza (22b) | 1.5 | Yes | Yes |
| 5-H-10-Propargyl 5,10-dideaza (6b) | 12.0 | Yes | Yes |
| 5-Me-10-Propargyl 5,10-dideaza (14b) | 1.5 | Yes | Yes |
| 5-Me-10-Allyl 5,10-dideaza (13b) | 3.0 | Yes | Yes |
| MTX | 9.0 | Yes | Yes |

The results show the deazaaminopterin compounds on a similar dosage level are able to reduce the inflammation of the mouse paw and visibly decrease the swelling of the rear paws. Results are similar to those obtained by visual observation of the effect of methotrexate which also reduced inflammation and decreases the swelling. The anti-arthritic activity of the deazaaminopterin compounds tested was confirmed by the results.

EXAMPLE 22

In Vivo Biology Of Type II Collagen Arthritis And Methotrexate Treatment Using Heteroaroyl 5-Deazaaminopterins and 5,10-Dideazaminopterins The following data illustrate administration to mice of compounds of the invention compared to methotrexate in the evaluation of anti-inflammatory activity. The data are presented as the caliper-measured degree of swelling of the rear paws of the mouse.

The efficacy evaluation used a mouse model of inflammatory disease that occurs in response to an antigenic challenge with Type II collagen as described in Example 20 hereinabove.

The effect of methotrexate and tested compounds on the extent of inflammation was determined by direct analysis of paw swelling using caliper measurements. The results are presented in Table 7, and show a direct correlation between the decrease in the number of animals having disease and a decrease in the extent of inflammation, as determined by paw swelling.

TABLE 7

Antiarthritic Effect of Heteroaroyl Deazaminopterins

| COMPOUND | DOSE (mg/kg) | NO MICE AFFECTED ON DAY INDICATED[b] | | | AVG. THICKNESS OF REAR PAWS (MM) DAYS 30–44 | |
|---|---|---|---|---|---|---|
| | | DAY 30 | DAY 37 | DAY 44 | TREATED[c,d] | UNTREATED[c,d] |
| None | — | 31/43 | 38/43 | 41/43 | — | 2.29–2.73 |
| 29 | NT | | | | | |
| 39 | 6.0 | 0/5 | 2/5 | 2/5 | 2.19–2.33 | |
| 40 | 6.0 | 0/8 | 1/8 | 3/8 | 2.13–2.27 | |
| 47 | 6.0 | 2/8 | 4/8 | 7/8 | 2.13–2.32 | |
| 49 | NT | | | | | |
| 75 | 8.0 | 2/8 | 7/8 | 7/8 | 2.19–2.63 | |
| 97 | 12.0 | 5/8 | 7/8 | 7/8 | 2.28–2.67 | |
| 103 | NT | | | | | |
| MTX[a] | 9.0 | 1/22 | 1/22 | 6/22 | 2.128–2.34 | |

[a]. MTX and untreated controls are composites from multiple runs.
[b]. Visual evidence of inflammation.
[c]. Values in parentheses are 30 day and 44 day measurements vs. equivalent for untreated controls; decrease in inflammation vs. control is most notable at day 44.
[d]. 2.14–2.20 nm represents normal hind paws thickness of age-matched control mice.
NT Not tested It is apparent from the above results that the number of test mice affected was very considerably decreased by administration of heteroaroyl-5-deazaaminopterin or 5,10-dideazaaminopterin compared when compared to untreated controls. The results show that heteroaroyl-5-deazaaminopterin or 5,10-dideazaaminopterin compounds on a similar dosage level to be at least as effective as methotrexate, and since methotrexate is accepted as an effective antiarthritic drug, the 5-deazaaminopterin or 5,10-dideazaaminopterin compounds are expected to be at least as effective as methotrexate under similar conditions. The potent antiarthritic activity of the heteroaroyl-5-deazaaminopterin or 5,10-dideazaaminopterin compounds tested is evident from the results.

EXAMPLE 23

Effect of Deazaaminopterins on Growth of Murine Leukemia Cells

This example illustrates the evaluation of the effect of 5-deazaaminopterins on growth inhibition of L 1210 murine leukemia cells in culture derived from L 1210.

Murine L 1210 cells were obtained as intraperitoneal ascites suspensions from $BD2F_1$ mice. The cells were grown in RPM1 1640 medium supplemented with 10% fetal calf serum. Cultures in the logarithmic stage of growth were harvested, resuspended and exposed to test compounds at varying concentrations. Growth of controls was monitored to verify that the growth pattern was normal. At 72 hours, cell counts were taken and averaged and the means were plotted against drug concentration to determine the concentration causing 50% inhibition of cell growth.

The effect of test compound on growth inhibition of L 1210 leukemia cells was determined and compared with the effect of methotrexate. Results are shown in Table 8.

TABLE 8

Anticancer Activity of 5-Deaza and 5,10-Dideazaminopterins; Growth Inhibition of L1210 Cells

| | Compound | Cytotoxicity Inhibition of L1210 Growth (μM) |
|---|---|---|
| 1b | 5,10-DDA | 0.027 |
| 2b | 10-Me-5,10-DDA | 0.0075 |
| 3b | 10-et-5,10-DDA | 0.075 |
| 9b | 5-Me-5,10-DDA | 0.379 |
| 103 | 5-Me-5,10-Dideaza-3'-azaaminopterin | 0.629 |
| 13b | 5-Me-10-allyl-5,10-DDA | 0.009 |
| 39 | 5-Me-2',5'-thienyl-5-DA | 0.025 |
| 21a | 5-Pr-5-DA | 0.0065 |
| 12a | 5-Me-10-Pr-5-DA | 0.011 |
| | MTX | 0.019 |

DA means deazaaminopterin.
DDA means dideazaaminopterin.

What is claimed is:

1. 5-deazaaminopterin and 5,10-dideazaaminopterin compound of the formula

[Structural formula I showing pteridine core with NH₂, R₁, CH₂—A—X—NHCH(COOH)CH₂CH₂COOH substituents]

wherein A is N and X is selected from the group consisting of

[Three thienyl-carbonyl structures shown]

wherein $R_1$ is hydrogen or alkyl having from one to eight carbon atoms; and $R_2$ is hydrogen, alkyl having from one to eight carbon atoms, or alkenyl or alkynyl having from three to eight carbon atoms.

2. 5-deazaaminopterin and 5,10-dideazaaminopterin compounds of the formula

[Structural formula (I)]

wherein A is N;
X is

[phenyl-carbonyl structure]

$R_1$ is hydrogen;
$R_2$ is alkenyl or alkynyl having from four to eight carbon atoms.

3. The compounds of claim 1 wherein $R_1$ is hydrogen or alkyl having from one to three carbon atoms, and $R_2$ is hydrogen or alkyl having from one to three carbon atoms, or alkenyl or alkynyl having from three to five carbon atoms.

4. The compound of claim 1 wherein X is

[thienyl-carbonyl structure]

A is N, $R_1$ is methyl, and $R_2$ is hydrogen, namely 5-methyl-5-deaza-2',5'-thienylaminopterin.

5. The compounds of claim 1 wherein X is

[thienyl-carbonyl structure]

A is N, $R_1$ is methyl and $R_2$ is methyl, namely 5-methyl-5-deaza-2',5'-thienylmethothrexate.

6. A method of treating arthritis comprising administering to a warm-blooded animal having an inflammation of the joints or other evidence of the arthritis, a therapeutic and nontoxic amount of a 5-deazaaminopterin or 5,10-dideazaaminopterin compound of the formula

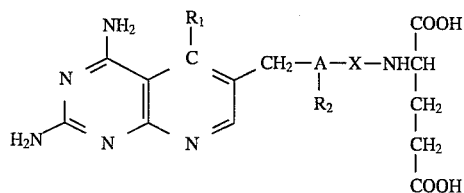

wherein A is CH or N;
X is selected from the group consisting of

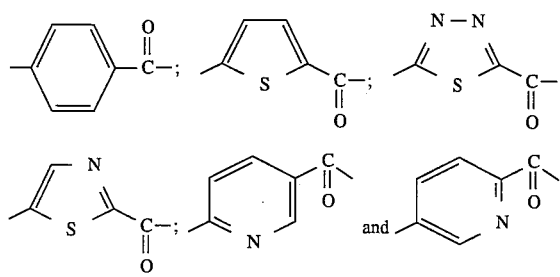

R₁ is hydrogen or alkyl, having from one to eight carbon atoms; and
R₂ is hydrogen or alkyl, alkenyl, or alkynyl having from one to eight carbon atoms.

7. 5-deazaaminopterin and 5,10-dideazaaminopterin compounds of the formula

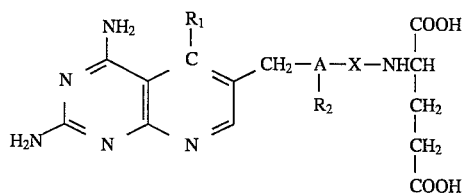

wherein A is N;
X is

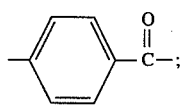

R₁ is alkyl having from one to eight carbon atoms;
R₂ alkenyl, or alkynyl having from four to eight carbon atoms.

8. 5-deazaaminopterin and 5,10 -dideazaaminopterin compound of the formula

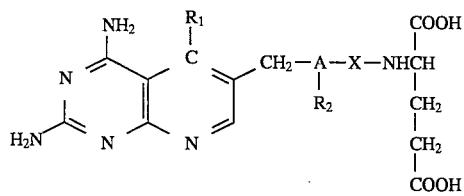

wherein X is

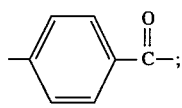

A is N, R₁ is methyl, and R₂ is propenyl, namely 5-methyl-10-allyl-5-deazaaminopterin.

9. 5-deazaaminopterin and 5,10-dideazaaminopterin compounds of the formula

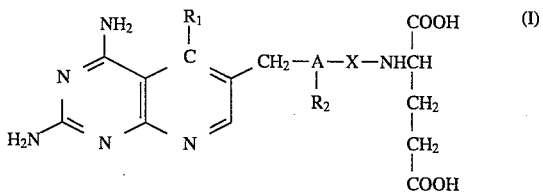

wherein A is CH;
X is

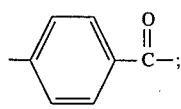

R₁ is hydrogen; and
R₂ is alkenyl or alkynyl having from four to eight carbon atoms.

10. The method of claim 6 wherein the compound is administered in an amount within the range from about 0.1 to about 500 mg per day.

11. 5-deazaaminopterin and 5,10 -dideazaaminopterin compound of the formula

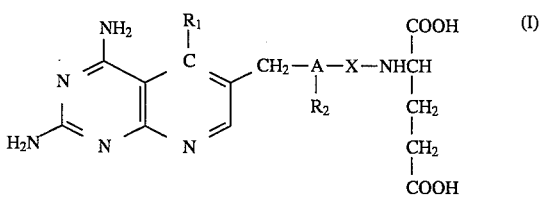

wherein X is

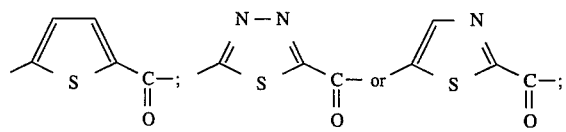

and A is CH, and R₁ and R₂ are independently hydrogen, alkyl having from one to eight carbon atoms, alkenyl or alkynyl having from three to eight carbon atoms.

12. 5-deazaaminopterin and 5,10 -dideazaaminopterin compound of the formula

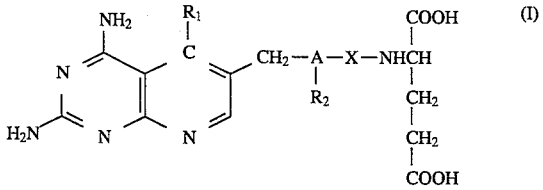

wherein X is

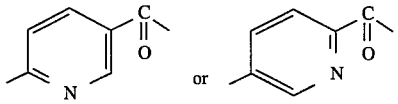

and A is CH, and R₁ is hydrogen or alkyl having from one to eight carbon atoms, and R₂ is hydrogen, alkyl having from one to eight carbon atoms, alkenyl or alkynyl having from three to eight carbon atoms.

13. The compounds of claim 1 wherein X is

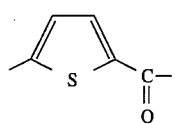

A is N, $R_1$ is ethyl and $R_2$ is methyl, namely 5-ethyl-5-deaza-2',5'-thienylmethotrexate.

14. The method of claim 6 wherein the administered compound is 5-propyl-5-deazaaminopterin.

15. The method of claim 6 wherein the administered compound is 5-methyl-10-propargyl-5-deazaaminopterin.

16. The method of claim 6 wherein the administered compound is 5-ethyl-5-deazamethotrexate.

17. The method of claim 6 wherein the administered compound is 5-methyl-5-deaza-2',5'-thienylaminopterin.

18. The method of claim 6 wherein the administered compound is 5-methyl-10-propyl-5-deazaaminopterin.

19. The method of claim 6 wherein the administered compound is 10-methyl-5,10-dideazaaminopterin.

20. The method of claim 6 wherein the compound is administered as a pharmaceutically acceptable salt thereof.

21. The method of claim 10 wherein the administered compound is 5-propyl-5-deazaaminopterin.

22. The method of claim 10 wherein the administered compound is 5-methyl-10-propyl-5-deazaaminopterin.

23. The method of claim 10 wherein the administered compound is 5-methyl-10-allyl-5,10-dideazaaminopterin.

24. The method of claim 18 wherein the administered compound is 5-methyl-2',5'-thienyl-5-deazaaminopterin.

* * * * *